(12) United States Patent      (10) Patent No.: US 8,999,661 B2
Kung et al.      (45) Date of Patent: Apr. 7, 2015

(54) COMPOSITIONS FOR DETECTING CELL DEATH AND METHODS OF USE THEREOF

(75) Inventors: Andrew Kung, Walpole, MA (US); Pallab Banerjee, Roslindale, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 664 days.

(21) Appl. No.: 12/511,478

(22) Filed: Jul. 29, 2009

(65) Prior Publication Data

US 2010/0034800 A1    Feb. 11, 2010

Related U.S. Application Data

(60) Provisional application No. 61/084,861, filed on Jul. 30, 2008.

(51) Int. Cl.
*C12Q 1/32* (2006.01)
*G01N 33/50* (2006.01)
*C07K 14/00* (2006.01)
*C12N 9/04* (2006.01)

(52) U.S. Cl.
CPC .............. *C12Q 1/32* (2013.01); *G01N 33/5011* (2013.01); *G01N 2510/00* (2013.01)

(58) Field of Classification Search
USPC ............................ 435/190, 69.7, 26; 530/350
See application file for complete search history.

(56) References Cited

U.S. PATENT DOCUMENTS

| | | | |
|---|---|---|---|
| 4,873,316 | A | 10/1989 | Meade et al. |
| 5,223,409 | A | 6/1993 | Ladner et al. |
| 5,284,656 | A | 2/1994 | Platz et al. |
| 5,403,484 | A | 4/1995 | Ladner et al. |
| 5,422,266 | A | 6/1995 | Cormier et al. |
| 5,451,569 | A | 9/1995 | Wong et al. |
| 5,571,698 | A | 11/1996 | Ladner et al. |
| 2003/0059893 | A1 | 3/2003 | Ladunga et al. |
| 2004/0067503 | A1* | 4/2004 | Tan et al. ........................... 435/6 |
| 2004/0191843 | A1 | 9/2004 | Wright et al. |
| 2005/0171043 | A1* | 8/2005 | Mochly-Rosen et al. ...... 514/44 |
| 2007/0197430 | A1 | 8/2007 | Baell et al. |
| 2010/0111856 | A1 | 5/2010 | Herman et al. |

FOREIGN PATENT DOCUMENTS

| EP | 0264166 | 4/1988 |
|---|---|---|
| WO | WO 2007/021621 A2 | 2/2007 |
| WO | WO 2014/011327 A1 | 1/2014 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Kurisaki et al., Biochemical and Biophysical Research Communications 335:667-675, 2005.*
Halliwell et al., Biosensors and Bioelectronics 17:965-972, 2002.*
Weijers et al.., Clin. Chem. 36(1):59-64, 1990.*
Chen et al., Journal of Molecular Catalysis B: Enzymatic 16:283-291, 2002.*
Abuchowski et al., (1981) "Soluble polymer-enzyme adducts" In: *Enzymes as Drugs* Holcenberg et al., eds., Wiley-Interscience, New York, NY, p. 367-383.
Adjei et al., (1990) *Pharmaceutical Research* 7(6):565 569: "Pulmonary delivery of peptide drugs: effect of particle size on bioavailability of leuprolide acetate in healthy male volunteers.".
Adjei et al., (1990) *International Journal of Pharmaceutics* 61:135-144: "Bioavailability of leuprolide following intratracheal administration to beagle dogs.".
Amann et al., (1988) *Gene* 69:301-315: "Tightly regulated tac promoter vectors useful for the expression of unfused and fused proteins in *Escherichia coli.* ".
Baldari et al., (1987) *Embo J* 6:229-234: "A novel leader peptide which allows efficient secretion of a fragment of human interleukin 1β in *Saccharomyces cerevisiae.* ".
Banaszak et al., (1975) "Malate dehydrogenases" In: Boyer PD (Ed.), *The Enzymes*, 3rd ed., vol. 11, Academic Press, New York. p. 369-396.
Banerji et al., (1983) *Cell* 33:729-740: "A lymphocyte-specific cellular enhancer is located downstream of the joining region in immunoglobulin heavy chain genes.".
Batra et al., (2002) *Curr Opin Biotechnol* 13: 603-8: "Pharmacokinetics and biodistribution of genetically engineered antibodies.".
Bialik et al., (2008) *Adv Exp Med Biol* 615:177-200: "Autophagy and tumor suppression: recent advances in understanding the link between autophagic cell death pathways and tumor development.".
Birnbaum et al., (1994) *J Virol* 67:2521-2528: "An apoptosis-inhibiting gene from a nuclear polyhedrosis virus encoding a polypeptide with Cys-His sequence motifs.".
Braquet et al. (1989) *Journal of Cardiovascular Pharmacology* 13(suppl. 5):143-146: "Effect of endothelin-1 on blood pressure and bronchopulmonary system of the guinea pig.".

(Continued)

*Primary Examiner* — Delia Ramirez
(74) *Attorney, Agent, or Firm* — Wolf, Greenfield & Sacks, P.C.

(57) ABSTRACT

The invention provides compounds and methods of their use in the detection of apoptosis and necrosis both in vitro and in vivo. Also provided are compounds and methods of their use in selective delivery of agents to cells undergoing apoptosis or necrosis. The compounds and methods are based on conjugates formed with a dehydrogenase such as lactate dehydrogenase, alcohol dehydrogenase, aldehyde dehydrogenase, and malate dehydrogenase. The compounds and methods are useful in the diagnosis and treatment of conditions characterized by apoptosis, including cancer, cardiac disease, neurologic disease including stroke, and autoimmunity. The compounds and methods offer distinct advantages over corresponding compounds and methods based on Annexin V. Also provided are methods for screening for compounds that modulate, i.e., inhibit or promote, apoptosis.

11 Claims, 11 Drawing Sheets

(56) References Cited

OTHER PUBLICATIONS

Brooks et al., (1999) *Proc Natl Acad Sci U S A* Feb. 2;96(3):1129-34: "Role of mitochondrial lactate dehydrogenase and lactate oxidation in the intracellular lactate shuttle.".
Bullok et al., (2005) *J Med Chem* Aug. 25 48(17):5404-7: "Synthesis and characterization of a small, membrane-permeant, caspase-activatable far-red fluorescent peptide for imaging apoptosis.".
Byrne et al., (1989) *Proc. Natl. Acad. Sci. U S A* 86:5473-5477: "Multiplex gene regulation: a two-tiered approach to transgene regulation in transgenic mice.".
Calame et al., (1988) *Adv. Immunol.* 43:235-275: "Transcriptional controlling elements in the immunoglobulin and T cell receptor loci.".
Camper et al., (1989) *Genes Dev.* 3:537-546: "Postnatal repression of the a-fetoprotein gene is enhancer independent.".
Carell et al., (1994) *Angew Chem Int Ed Engl* 33:2059-2061: "A novel procedure for the synthesis of libraries containing small organic molecules.".
Carell et al., (1994) *Angew Chem Int Ed Engl* 33:2061-2064: "A solution-phase screening procedure for the isolation of active compounds from a library of molecules.".
Catley et al., (2003) *Blood* 102:2615-22: "NVP-LAQ824 is a potent novel histone deacetylase inhibitor with significant activity against multiple myeloma.".
Chang et al., *Arch Biochem Biophys*, 2003. 411: 63-72: "Mice lacking inducible nitric oxide synthase show strong resistance to anti-Fas antibody-induced fulminant hepatitis.".
Cho et al., (1993) *Science* 261:1303: "An unnatural biopolymer.".
Crabb et al., (2004) *The Proceedings of the Nutrition Society* 63(1): 49-63: "Overview of the role of alcohol dehydrogenase and aldehyde dehydrogenase and their variants in the genesis of alcohol-related pathology.".
Crook et al., (1993) *J Virol* 67:2168-2174: "An apoptosis-inhibiting baculovirus gene with a zinc finger-like motif.".
Cull et al., (1992) *Proc Natl Acad Sci U S A* 89:1865-1869: "Screening for receptor ligands using large libraries of peptides linked to the c terminus of the Lac repressor.".
Cummings et al., (2004) *Biochim Biophys Acta* 1705:53-66: "Apoptosis pathway-targeted drugs—from the bench to the clinic.".
Cwirla et al., (1990) *Proc Natl Acad Sci USA* 87:6378-6382: "Peptides on phage: a vast library of peptides for identifying ligands.".
Debatin, (2004) *Cancer Immunol Immunother* Mar;53(3):153-9. Epub Jan. 29, 2004: "Apoptosis pathways in cancer and cancer therapy.".
Debs et al., (1988) *J Immunol* 140:3482-3488: "Lung-specific delivery of cytokines induces sustained pulmonary and systemic immunomodulation in rats.".
Degterev et al., (2003) *Oncogene* Nov. 24;22(53):8543-67: "A decade of caspases.".
Deveraux et al., (1999) *Genes Dev* 13:239-252: "IAP family proteins—suppressors of apoptosis.".
Devlin et al., (1990) *Science* 249:404-406: "Random peptide libraries: a source of specific protein binding molecules.".
Dewitt et al., (1993) *Proc Natl Acad Sci U S A* 90:6909: "Diversomers: An approach to nonpeptide, nonoligomeric chemical diversity.".
Edlund et al., (1985) *Science* 230:912-916: "Cell-specific expression of the rat insulin gene: evidence for role of two distinct 5' flanking element.".
Erb et al., (1994) *Proc Natl Acad Sci U S A* 91:11422: "Recursive deconvolution of combinatorial chemical libraries.".
Felici et al., (1991) *J Mol Biol* 222:301-310: "Selection of antibody ligands from a large library of oligopeptides expressed on a multivalent exposition vector.".
Feng et al., (2000) *J Clin Invest* 105: 329-39: "Colchicine protects mice from the lethal effect of an agonistic anti-Fas antibody.".
Fodor et al., (1993) *Nature* 364:555-556: "Multiplexed biochemical assays with biological chips.".

Freedman et al., (2002) *Proc Natl Acad Sci U S A* 99: 5367-72: "Structural basis for recruitment of CBP/p300 by hypoxia-inducible factor-1 alpha.".
Fu et al., (2006) *Bioconjugate Chem* 17:1043-1056: "Dendritic iodinated contrast agents with peg-cores for CT imaging: Synthesis and preliminary characterization.".
Gallop et al., (1994) *J Med Chem* 37:1233: "Applications of combinatorial technologies to drug discovery. 1. Background and peptide combinatorial libraries.".
Gottesman, (1990) Gene Expression Technology: Methods in Enzymology 185, Academic Press, San Diego, Calif. p. 119-128.
Gross et al., (2005) *Cancer Cell* Jan;7(1):5-15: "Spying on cancer: molecular imaging in vivo with genetically encoded reporters.".
Hanahan et al., (2000) *Cell* Jan. 7;100(1):57-70: "The hallmarks of cancer.".
Holmes, (1972) *FEBS Lett* 28:51-55: "Evolution of lactate dehydrogenase genes.".
Houghten et al., (1992) *Bio/Techniques* 13:412-421: "The use of synthetic peptide combinatorial libraries for the identification of bioactive peptides.".
Hubbard et al., (1989) *Annals of Internal Medicine* 3:206-212: "Anti-neutrophil-elastase defenses of the lower respiratory tract in α1-antitrypsin deficiency directly augmented with an aerosol of α1-antitrypsin.".
Kaufman et al., (1987) *Embo J* 6:187-195: "Translation efficiency of polycistronic mRNAs and their utilization to express heterologous genes in Mammalian Cells.".
Kessel and Gruss, (1990) *Science* 249:374-379: "Murine developmental control genes.".
Kung et al., (2000) *Nat Med* 6: 1335-40: "Suppression of tumor growth through disruption of hypoxia-inducible transcription.".
Kurjan and Herskowitz., (1982) *Cell* 30:933-943: "Structure of a yeast pheromone gene (MFα): A putative α-factor precursor contains four tandem copies of mature α-factor.".
Lahorte et al., (2004) *Eur J Nucl Med Mol Imaging* Jun;31(6):887-919. Epub May 12, 2004: "Apoptosis-detecting radioligands: current state of the art and future perspectives.".
Lam (1997) *Anticancer Drug Des* 12:145: "Application of combinatorial library methods in cancer research and drug discovery.".
Lam et al., (1991) *Nature* 354:82-84: "A new type of synthetic peptide library for identifying ligand-binding activity.".
Langer, (1990) *Science* 249:1527-1533: "New methods of drug delivery.".
Laxman et al., (2002) *Proc Natl Acad Sci U S A* Dec. 24;99(26):16551-5. Epub Dec. 10, 2002: "Noninvasive real-time imaging of apoptosis.".
Li et al., (1983) *J Biol Chem* 258:7029-7031: "Evolutionary relationships of vertebrate lactate dehydrogenase isozymes A4 (muscle), B4 (heart), and C4 (testis).".
Luckow and Summers, (1989) *Virology* 170:31-39: "High level expression of nonfused foreign genes with Autographa californica nuclear polyhedrosis virus expression vector.".
Markert et al., (1975) *Science* 189:102-114: "Evolution of a gene.".
Massoud et al., (2003) *Genes Dev* Mar. 1;17(5):545-80: "Molecular imaging in living subjects: seeing fundamental biological processes in a new light.".
Messerli et al., (2004) *Neoplasia* Mar.-Apr.;6(2):95-105: "A novel method for imaging apoptosis using a caspase-1 near-infrared fluorescent probe.".
Michalet et al., (2005) *Science* 307:538-544: "Quantum dots for live cells, in vivo imaging, and diagnostics.".
Newmark et al., (1982) *J Appl Biochem* 4:185-189: "Preparation and properties of adducts of streptokinase and streptokinase-plasim complex with polyethylene glycol and pluronic polyol F38.".
Nishimura et al., (1997) *Int Immunol* 9: 307-16: "In vivo analysis of Fas antigen-mediated apoptosis: effects of agonistic anti-mouse Fas mAb on thymus, spleen and liver.".
Ntziachristos et al., (2002) *Nat Med* Jul;8(7):757-60. Epub Jun. 24, 2002: "Fluorescence molecular tomography resolves protease activity in vivo.".

(56) References Cited

OTHER PUBLICATIONS

Oeswein et al., (1990) "Aerosolization of Protein Pharmaceuticals", In: Proceedings of Symposium on Respiratory Drug Delivery II, Keystone, Colorado, Mar. 1990.
Ogasawara et al., (1993) *Nature* 364: 806-9: "Lethal effect of the anti-Fas antibody in mice.".
Pinkert et al., (1987) *Genes Dev.* 1:268-277: "An albumin enhancer located 10 kb upstream functions along with its promoter to direct efficient, liver-specific expression in transgenic mice.".
Prasher et al., (1992) *Gene* 111:229-233: "Primary structure of the Aequoria victoria green fluorescent protein.".
Queen and Baltimore, (1983) *Cell* 33:741-748: "Immunoglobulin gene transcription is activated by downstream sequence elements.".
Rubin et al., (2003) *Proc Natl Acad Sci U S A* 100: 13513-8: "A small-molecule antagonist of CXCR4 inhibits intracranial growth of primary brain tumors.".
Sambrook et al., eds., (1989) Chapter 16, Molecular Cloning: A Laboratory Manual, 2nd ed., Cold Spring Harbor Laboratory, Cold Spring Harbor Laboratory Press, Cold Spring Harbor, N.Y.
Sambrook et al., eds., (1989) Chapter 17, Molecular Cloning: A Laboratory Manual, 2nd ed., Cold Spring Harbor Laboratory, Cold Spring Harbor Laboratory Press, Cold Spring Harbor, N.Y.
Sawhney et al., (1993) *Macromolecules* 26:581-587: "Bioerodible hydrogels based on photopolymerized poly(ethylene glycol)-co-poly(α-hydroxy acid) diacrylate macromers.".
Schmitt, (2003) *Nat Rev Cancer* Apr;3(4):286-95: "Senescence, apoptosis and therapy—cutting the lifelines of cancer.".
Schultz et al., (1987) *Gene* 54:113-123: "Expression and secretion in yeast of a 400-kDa envelope glycoprotein derived from Epstein-Barr virus.".
Scott and Smith, (1990) *Science* 249:386-390: "Searching for peptide ligands with an epitope library.".
Seed, (1987) *Nature* 329:840: "An LFA-3 cDNA encodes a phospholipid-linked membrane protein homologous to its receptor CD2.".
Shah et al., (2005) *Mol Ther* Jun;11(6):926-31: "In vivo imaging of S-TRAIL-mediated tumor regression and apoptosis.".
Shaner et al., (2005) *Nat Methods* 2:905-909: "A guide to choosing fluorescent proteins.".
Shcherbo et al., (2007) *Nat Methods* 4:741-6: "Bright far-red fluorescent protein for whole-body imaging.".
Smit et al., (1988) *Clin Chem* 34: 2475-80: "Catabolism of circulating enzymes: plasma clearance, endocytosis, and breakdown of lactate dehydrogenase-1 in rabbits.".
Smith and Johnson, (1988) *Gene* 67:31-40: "Single-step purification of polypeptides expressed in *Escherichia coli* as fusions with glutathione S-transferase.".
Smith et al. (1983) *Mol Cell Biol* 3:2156-2165: "Production of human beta interferon in insect cells infected with baculovirus expression vector.".
Smith et al. (1989) *J Clin Invest* 84:1145-1146: "Pulmonary deposition and clearance of aerosolized alpha-1-proteinase inhibitor administered to dogs and to sheep.".
Sommer et al., (2003) *Oncogene* 22:4266-4280: "Inhibitor of apoptosis protein (IAP) survivin is upregulated by oncogenic c-H-Ras.".
Studier et al., (1990) Gene Expression Technology: Methods in Enzymology 185, Academic Press, San Diego, Calif. p. 60-89.
Sudo et al., (1992) *Hum Genet* 89: 158-62: "Molecular characterization of genetic mutations in human lactate dehydrogenase (LDH) B(H) variant.".
Tait et al., (2004) *Anal Biochem* 329: 112-9: "Measurement of the affinity and cooperativity of annexin V-membrane binding under conditions of low membrane occupancy.".
Takeno et al., (1989) *Biochem J* 257:921-924: "Structure of the human lactate dehydrogenase B Gene.".
Tang et al., (2005) *Cancer Res* 65: 8324-30: "In vivo assessment of RAS-dependent maintenance of tumor angiogenesis by real-time magnetic resonance imaging.".
Thie, (2004) *J. Nucl Med* 45(9): 1431-34: "Understanding the standardized uptake value, its methods, and implications for usage.".
Toretsky et al., (2004) *Nuclear Med Biol* 31:747-752, 50: "Preparation of F-18 labeled annexin Va potential PET radiopharmaceutical for imaging cell death.".
Visser et al., (2009) *J Nucl Med* 50: 139-47: "Spatial resolution and sensitivity of the inveon small-animal PET scanner.".
Wada et al., (1992) *Nucleic Acids Res.* 20:2111-2118: "Codon usage tabulated from the GenBank genetic sequence data.".
Walensky et al., (2004) *Science* 305:1466-70: "Activation of apoptosis in vivo by a hydrocarbon-stapled BH3 helix.".
Walensky, (2006) *Cell Death Differ* 13:1339-50: "BCL-2 in the crosshairs: tipping the balance of life and death.".
Weintraub et al., (1986) *Trends in Genetics*, vol. 1(1): 22-25 "Antisense RNA as a molecular tool for genetic analysis.".
Wilson et al., (1985) *Proc Natl Acad Sci U S A* 82: 5255-9: "Identical short peptide sequences in unrelated proteins can have different conformations: A testing ground for theories of immune recognition.".
Winoto et al., (1989) *Embo J.* 8:729-733: "A novel, inducible and T cell-specific enhancer located at the 3' end of the T cell receptor α locus.".
Zuckermann et al. (1994) *J Med Chem* 37:2678-85: "Discovery of nanomolar ligands for 7- transmembrane G-protein-coupled receptors from a diverse N-(substituted)glycine peptoid library.".
Bijsterbosch et al., Plasma clearance and endocytosis of cytosolic malate dehydrogenase in the rat. Biochem J. Feb. 15, 1983;210(2):419-28.
Bijsterbosch et al., Several dehydrogenases and kinases compete for endocytosis from plasma by rat tissues. Biochem J. Jul. 15, 1985;229(2):409-17.
Cho et al., Induction of apoptosis by selenite and selenodiglutathione in HL-60 cells: correlation with cytotoxicity. Biochem Mol Biol Int. May 1999;47(5):781-93.
Chuang et al., Glyceraldehyde-3-phosphate dehydrogenase, apoptosis, and neurodegenerative diseases. Annu Rev Pharmacol Toxicol. 2005;45:269-90.
Fotakis et al., In vitro cytotoxicity assays: comparison of LDH, neutral red, MTT and protein assay in hepatoma cell lines following exposure to cadmium chloride. Toxicol Lett. Jan. 5, 2006;160(2):171-7. Epub Aug. 18, 2005.
GENBANK Submission; NIH/NCBI, Accession No. NM_000667. Zuo et al., Dec. 7, 2009. 4 pages.
GENBANK Submission; NIH/NCBI, Accession No. NM_000668. Ross et al., Dec. 6, 2009. 6 pages.
GENBANK Submission; NIH/NCBI, Accession No. NM_000669. Ross et al., Dec. 6, 2009. 5 pages.
GENBANK Submission; NIH/NCBI, Accession No. NM_002300. de Haas et al., Sep. 20, 2009. 4 pages.
GENBANK Submission; NIH/NCBI, Accession No. NM_002301. Tang et al., Sep. 13, 2009. 4 pages.
GENBANK Submission; NIH/NCBI, Accession No. NM_005566. Sudhakaran et al., Oct. 11, 2009. 6 pages.
GENBANK Submission; NIH/NCBI, Accession No. NM_005917. Lee et al., Jun. 21, 2009. 5 pages.
GENBANK Submission; NIH/NCBI, Accession No. NP_000658. Zuo et al., Dec 7, 2009. 4 pages.
GENBANK Submission; NIH/NCBI, Accession No. NP_000659. Ross et al., Dec. 6, 2009. 4 pages.
GENBANK Submission; NIH/NCBI, Accession No. NP_000660. Ross et al., Dec. 6, 2009. 4 pages.
GENBANK Submission; NIH/NCBI, Accession No. NP_002291. de Haas et al., Sep. 20, 2009. 3 pages.
GENBANK Submission; NIH/NCBI, Accession No. NP_002292. Tang et al., Sep. 13, 2009. 3 pages.
GENBANK Submission; NIH/NCBI, Accession No. NP_005557. Zhao et al., Dec. 6, 2009. 4 pages.
GENBANK Submission; NIH/NCBI, Accession No. NP_005908. Lee et al., Jun. 21, 2009. 4 pages.
Rose et al., Hydrogen sulfide protects colon cancer cells from chemopreventative agent beta-phenylethyl isothiocyanate induced apoptosis. World J Gastroenterol. Jul. 14, 2005;11(26):3990-7.
Rospert et al., Protein translocation into mitochondria. Cell Biology. Jan 1, 2006;2:253-8.

(56) References Cited

OTHER PUBLICATIONS

Schmitz, Reversible nuclear translocation of glyceraldehyde-3-phosphate dehydrogenase upon serum depletion. Eur J Cell Biol. Jun. 2001;80(6):419-27.

Shashidharan et al., Nuclear translocation of GAPDH-GFP fusion protein during apoptosis. Neuroreport. Apr. 6, 1999;10(5):1149-53.

Smit et al., Receptor-mediated endocytosis of lactate dehydrogenase M4 by liver macrophages: a mechanism for elimination of enzymes from plasma. Evidence for competition by creatine kinase MM, adenylate kinase, malate, and alcohol dehydrogenase. J Biol Chem. Sep. 25, 1987;262(27):13020-6.

[No Author Listed], Protein labeling technology kits. BioPAL, Inc. Downloaded from http://www.biopal.com on Mar. 5, 2012. One page.

Meijs et al., A facile method for the labeling of proteins with zirconium isotopes. Nucl Med Biol. May 199623(4):439-48.

* cited by examiner

*In vivo* imaging of cell death in a therapeutic model

Control

AMN107

COMPOSITIONS FOR DETECTING CELL DEATH AND METHODS OF USE THEREOF

RELATED APPLICATIONS

This application claims a benefit of and priority under 35 U.S.C. §119 to U.S. Provisional Application No. 61/084,861, filed Jul. 30, 2008, the contents of which are herein incorporated by reference in their entirety.

BACKGROUND OF THE INVENTION

Cell death is a feature of many diseases as well as therapeutic methods, for example in the treatment of cancer. It is therefore desirable to be able to measure cell death, to assess either the status of a disease that involves cell death or the effect of a treatment that induces cell death. In recent years two distinct mechanisms of cell death known as apoptosis and necrosis have been described. While distinct in certain aspects, these two forms of cell death can also be viewed as extremes along a continuum, such that late-stage apoptosis overlaps with necrosis.

Apoptosis, which is also known as programmed cell death, is generally characterized as an energy-dependent, genetically controlled process by which cell death is activated through an internally regulated suicide program. Features of apoptosis generally include phosphatidylserine externalization, loss of membrane integrity, cytoplasm shrinkage, chromatin and nucleus condensation, DNA degradation, and fragmentation of the cell into smaller apoptotic bodies by a budding process. Normally the resulting apoptotic bodies are phagocytosed by macrophages and neighboring cells without inducing an inflammatory response. Methods frequently used to assess apoptosis include staining by fluorescently labeled annexin A5 (also known as Annexin V) and terminal uridine deoxynucleotidyl end-labeling (TUNEL) assay.

Necrosis, which is also known as accidental cell death, is typically induced by any of a variety of sudden, severe, non-physiological insults, for example physical, chemical, and ischemic insults. The process is generally characterized by progressive cell swelling, denaturation and coagulation of cytoplasmic proteins, disintegration of subcellular organelles and irreversible collapse of the plasma membrane integrity. This latter feature permits leakage of cytotoxic and other cellular components, inducing a local inflammatory response.

Loss of membrane integrity, a feature common to both apoptosis and necrosis, allows intracellular components to leak out of cells. As such, serum and plasma levels of intracellular components such as the lactate dehydrogenase (LDH) protein have been used as surrogate markers of cell death, i.e., necrosis and late-stage apoptosis.

SUMMARY OF THE INVENTION

The invention is based at least in part on the surprising discovery made by the inventors that dehydrogenase enzymes including LDH are, in addition to being leaked from dying cells, taken up and retained by dying cells. This uptake of dehydrogenases by dying cells makes it possible to detect and to monitor dying cells with suitably labeled dehydrogenase enzymes. In addition, this same uptake of dehydrogenases by dying cells also makes it possible to target those cells in a selective manner for delivery of agents provided as conjugates with dehydrogenases. Agents so delivered to dying cells can include therapeutic agents.

Compositions and methods of the invention described herein are useful for detecting and monitoring dying cells, both in vivo as well as in vitro. In one embodiment the invention is useful for detecting and monitoring cells undergoing apoptosis, including in particular, cells in early-stage apoptosis. The detecting and monitoring can be used to assess the status of a condition that is characterized by cell death, including specifically conditions characterized by apoptotic cell death. Alternatively or in addition, the detecting and monitoring can be used to assess the effect of a treatment that is characterized or accompanied by cell death, including specifically treatments that are characterized or accompanied by apoptotic cell death. For example, the detecting and monitoring can be used to assess the effect of chemotherapy and radiation therapy in the treatment of cancer.

Compositions and methods of the invention described herein are also useful for selectively delivering various agents, including therapeutic agents, to dying cells. In one embodiment the invention is useful for selectively delivering various agents, including therapeutic agents, to cells undergoing apoptosis, including in particular, cells in early-stage apoptosis.

Compositions and methods of the invention described herein are also useful for treating any of a variety of conditions characterized by cell death, including in particular apoptotic cell death. Such conditions can include conditions for which it is desired to reduce cell death and conditions for which it is desired to increase cell death.

The invention in one aspect is an isolated conjugate of a dehydrogenase linked to a detectable label, wherein the detectable label is not an immunoglobulin or dehydrogenase-binding fragment thereof.

In this and other aspects of the invention, in one embodiment the dehydrogenase is a lactate dehydrogenase (LDH). In this and other aspects of the invention, in one embodiment the dehydrogenase is a human LDH.

In this and other aspects of the invention, in one embodiment the dehydrogenase is an alcohol dehydrogenase (ADH). In this and other aspects of the invention, in one embodiment the dehydrogenase is a human ADH.

In this and other aspects of the invention, in one embodiment the dehydrogenase is an aldehyde dehydrogenase (ALDH). In this and other aspects of the invention, in one embodiment the dehydrogenase is a human ALDH.

In this and other aspects of the invention, in one embodiment the dehydrogenase is a malate dehydrogenase (MDH). In this and other aspects of the invention, in one embodiment the dehydrogenase is a human MDH.

In this and other aspects of the invention, in one embodiment the detectable label is selected from the group consisting of: a fluorescent label, a radioisotope, a nanoparticle, a chromophore, a dye, an enzyme, and a contrast agent, as well as any combination thereof. In this and other aspects of the invention, in one embodiment the detectable label is a fluorescent label. In this and other aspects of the invention, in one embodiment the detectable label is a radioisotope. In this and other aspects of the invention, in one embodiment the detectable label is a nanoparticle.

In this and other aspects of the invention, in one embodiment the invention is a composition including a conjugate of the invention. In one embodiment the composition is a pharmaceutical composition suitable for administration to a subject.

The invention in one aspect is an isolated conjugate of a dehydrogenase linked to at least one therapeutic agent. In this and other aspects of the invention, in one embodiment the therapeutic agent is an anti-apoptotic agent selected from the group consisting of: cyclocreatine, cyclocreatine phosphate, coenzyme Q10, L-carnitine, glutathione, α-lipoic acid, a caspase inhibiting peptide, and anti-apoptotic proteins or peptide fragments such as the inhibitor of apoptotic proteins (LAPs) and anti-apoptotic BCL-2 family members, as well as any combination thereof.

The invention in one aspect is polynucleotide encoding a dehydrogenase operably linked to a polynucleotide encoding a detectable label. In one embodiment the detectable label is a fluorescent protein. In one embodiment the detectable label is an enzyme.

In one aspect the invention is a vector containing a polynucleotide of the invention.

In one aspect the invention is a host cell containing a vector of the invention.

The invention in one aspect is a method for detecting cells undergoing cell death. The method according to this aspect of the invention includes the steps of contacting a test population of cells with a conjugate of a dehydrogenase linked to a detectable label, under conditions suitable for uptake of the conjugate by the test population of cells; and detecting the label in the test population of cells, wherein presence of the label in the test population of cells indicates cells undergoing cell death.

In this and other aspects of the invention, in one embodiment the cell death is apoptosis. In this and other aspects of the invention, in one embodiment the cell death is necrosis.

In this and other aspects of the invention, in one embodiment the method steps are carried out in vitro. In this and other aspects of the invention, in one embodiment the method steps are carried out ex vivo. In this and other aspects of the invention, in one embodiment at least one method step is carried out in vivo. In this and other aspects of the invention, in one embodiment the method steps are carried out in vivo.

In this and other aspects of the invention in one embodiment the test population of cells is obtained from a subject having or suspected of having a condition associated with apoptosis or necrosis.

In this and other aspects of the invention, in one embodiment the subject is a human.

In this and other aspects of the invention, in one embodiment the condition is selected from the group consisting of: cancer; chemotherapy-, radiation-, or hormone-induced apoptosis in solid and hematological tumors; tumor resistance to therapy; acute cardiac allograft rejection; acute myocardial infarction; anthracycline-induced cardiotoxicity; arrhytmogenic right ventricle dysplasia; skeletal muscle apoptosis; congestive heart failure; coronary artery disease; atherosclerosis; infectious endocarditis; myocarditis; myocardial dysfunction; myocardial ischemia-reperfusion injury; non-cardiac allograft rejection; graft-versus-host disease; bacterial infection; viral infection; multiple organ dysfunction syndrome; septic shock; cerebral ischemia-reperfusion injury, including stroke; macular degeneration; neurodegenerative disease; central nervous system trauma; autoimmune diabetes mellitus; rheumatoid arthritis; systemic lupus erythematosus; inflammatory bowel disease; multiple sclerosis; other autoimmune diseases; annexinopathies; osteoarthritis; renal failure; chronic renal atrophy and renal fibrosis; glomerular injury; and polycystic renal disease; as well as any combination thereof.

In one embodiment the method further includes the steps of measuring a test amount of label detected in the test population of cells; comparing the test amount of label detected in the test population to a reference amount of label detected in a reference population of cells; and determining (a) there is an increased amount of cell death when the test amount is greater than the reference amount, or (b) there is a decreased amount of cell death when the test amount is less than the reference amount.

The invention in one aspect is a method for treating a condition associated with apoptosis. The method according to this aspect of the invention includes the step of administering to a subject having or suspected to have a condition associated with apoptosis a pharmaceutical composition comprising a conjugate of a dehydrogenase linked to at least one therapeutic agent in an amount effective to treat the condition.

In one embodiment the method further includes the step of monitoring apoptosis in the subject.

The invention in one aspect is a method for selectively delivering an agent to an apoptotic cell. The method according to this aspect of the invention includes the step of contacting an apoptotic cell with a conjugate of a dehydrogenase linked to at least one agent.

In one embodiment the agent is an anti-apoptotic agent.

The invention in one aspect is a method for identifying an anti-apoptotic agent. The is method according to this aspect of the invention includes the steps of contacting a test cell with a test agent and a conjugate of a dehydrogenase linked to a detectable label, under conditions that otherwise induce apoptosis in the test cell; measuring a test amount of label in the test cell; comparing the test amount of label to a reference amount of label in a reference cell contacted with the conjugate under the conditions that otherwise induce apoptosis in the test cell; and identifying the test agent as an anti-apoptotic agent when the test amount of label is less than the reference amount of label.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

DETAILED DESCRIPTION OF THE INVENTION

Figure 1:
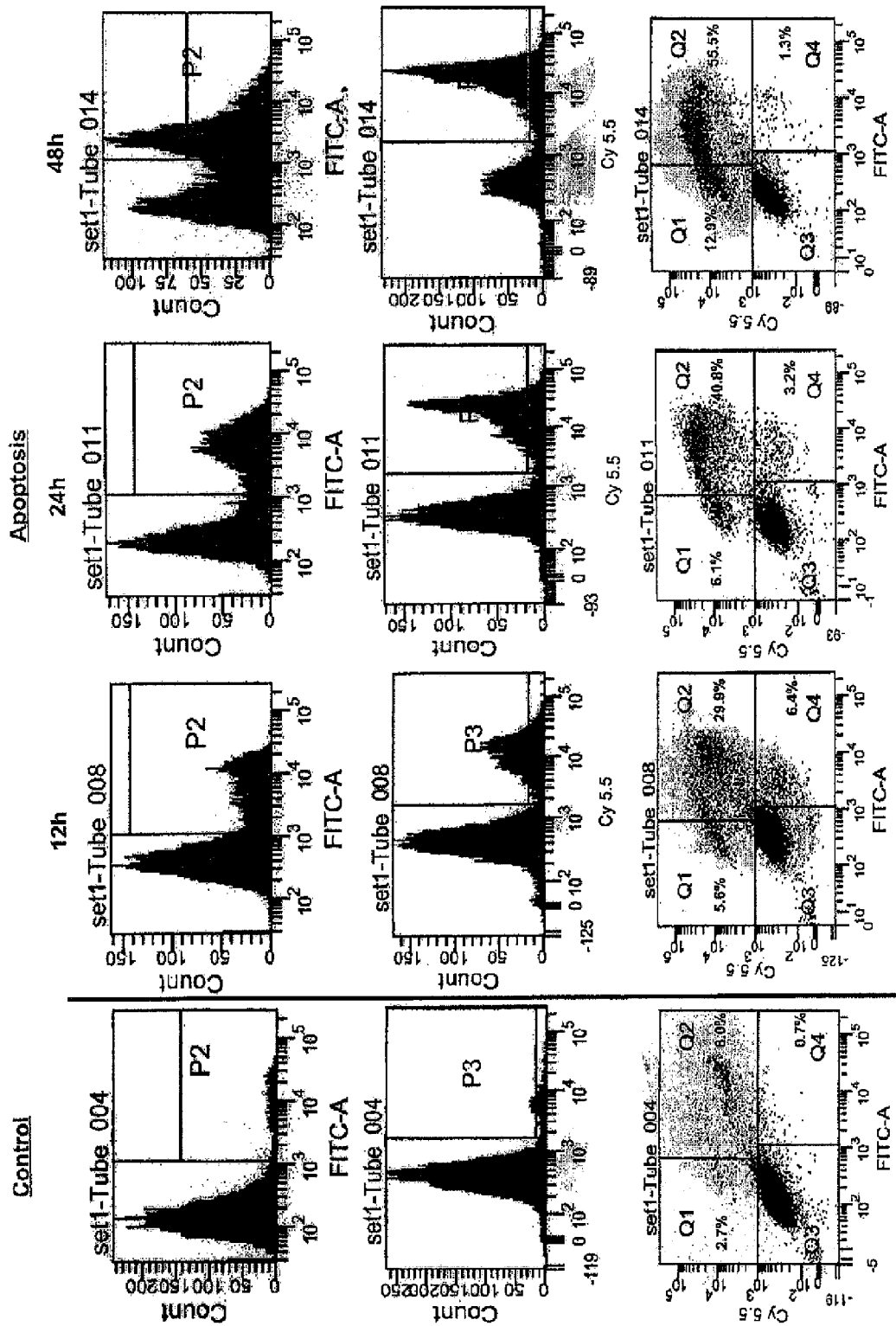
FIG. 1 is a collage of fluorescence-activated cell sorting (FACS) histograms depicting apoptosis over time in HeLa cells as measured using fluorescein isothiocyanate (FITC)-labeled Annexin V and Cy5.5-labeled LDH.

Apoptosis is a highly conserved form of programmed cell death (PCD) that plays an important role in multiple physiological processes like organ development, tissue homeostasis and regulation of the immune system since many organisms use this mechanism to selectively eliminate unwanted cells. However, when the physiological balance between survival and death signals tilts towards cell death, the apoptosis program is engaged and culminates in a variety of pathological conditions. Excessive apoptosis is known to result in progressive loss in tissue functionality, as occurs in acute myocardial infarction, chronic heart failure, allograft rejection, stroke, neurodegenerative disorders (e.g., Alzheimer's, Parkinson's and Huntington's disease) and inflammation. In contrast, autoimmune diseases like systemic lupus erythematosus (SLE) and rheumatoid arthritis are characterized by insufficient apoptosis, which enables immunologically competent cells (i.e., autoreactive lymphocytes) to survive and to injure healthy organs inappropriately. Anti-apoptotic mechanisms also play a critical role in cancer formation. Furthermore, the beneficial or detrimental effect of many drugs can be attributed to their action on the apoptotic process. Accordingly, non-invasive in vivo monitoring of the rate and extent at which apoptosis occurs may provide clinicians with relevant clinical information on disease activity and therapeutic efficacy.

Apoptosis can be divided into early- and late-stage apoptosis. Cells in early-stage apoptosis typically stain positive for Annexin V but do not stain positive for so-called vital stains such as propidium iodide (PI). In contrast, cells in late stage apoptosis, as well as necrotic cells, frequently stain positive for both Annexin V and PI.

A number of efforts, including clinical trials, have been made to measure apoptosis in vitro and in vivo. For the most part these studies have relied on various conjugates with Annexin V, which binds to phosphatidylserine. Annexin V is a member of the calcium and phospholipid binding superfamily of Annexin proteins, of which at least 13 members have been identified in a variety of organisms. Like the other Annexin members, Annexin V is widely expressed in eukaryotic organisms. The protein is mainly found intracellularly on the cytosolic side of plasma membranes, although very low concentrations (1-6 ng/ml) circulate in the blood compartment of healthy humans. Furthermore, the protein is ubiquitously expressed in a variety of cell types and tissues, including cardiomyocytes, vascular endothelium, erythrocytes, thrombocytes, lymphocytes, glial cells, astrocytes, oligodendrocytes, Schwann cells, skeletal muscle cells, hepatocytes, bronchi, chondrocytes, and osteoblasts.

Within the plasma membrane of live cells, phosphatidylserine (PS) residues are asymmetrically oriented such that they are exclusively exposed to the intracellular compartment, i.e., the PS residues face inward. Early in the apoptosis cascade, membrane polarity is lost, thus resulting in PS residues being exposed to the extracellular side of the plasma membrane. At this stage, Annexin V binds to the externally exposed PS residues, but the membrane is not freely permeable. Small molecular dyes, such as propidium iodide (PI) or trypan blue (i.e., vital dyes), cannot freely diffuse into cells. Thus, early apoptotic cells stain positive for Annexin V staining but negative for vital dye staining. In late apoptotic and necrotic cells, membrane integrity is lost, thus allowing vital dyes to freely diff-use into cells. Thus dead cells are both Annexin V and vital dye positive.

Based on these observations, Annexin V was originally labeled with different fluorescent tags (e.g., FITC) and is now routinely used for histological and cell-sorting studies to identify and quantify apoptotic cells. However, all of these detection methods (e.g., microscopy, immunohistochemistry, flow cytometry, high-throughput screening) are either characterized by is specific problems in detectability or exhibit restricted applicability in vitro and often require invasive sampling techniques like biopsies. Other methods like the TUNEL assay often lack sensitivity in quantifying the process since their detection mechanism only targets cells in a later stage of the apoptosis cascade, when phagocytosis of apoptotic cells is already occurring in vivo.

Annexin V has also been radiolabeled with radionuclide tags such as $^{99m}$Tc or $^{123}$I for non-invasive detection and quantification of apoptosis in vivo. Initial in vitro studies with normal and sickle-cell erythrocytes, activated blood platelets and tissue factor (TF)-expressing fibroblasts or ovarian carcinoma cells clearly demonstrated the proof of concept that early apoptosis could be detected successfully with radiolabeled Annexin V. Since then, extensive studies, including clinical trials, have been performed in the in vivo evaluation of radiolabeled Annexin V in animals and humans.

Results of these efforts to use tagged Annexin V to measure apoptosis have proven to be disappointing. The dynamic range afforded by these methods is quite limited, owing to the dampening effect of serum proteins on Annexin V binding and the requirement for calcium for Annexin V binding. In addition, Annexin V and related reagents are very expensive.

The invention is based at least in part on the ability of dehydrogenases to be taken up and retained by cells undergoing apoptosis and necrosis. It was previously reported that dying cells release enzymes including LDH. It was previously unknown, and unexpected, that dying cells also take up and retain LDH. In addition to LDH, it has also been discovered by the inventors that various other dehydrogenases, including at least alcohol dehydrogenase, aldehyde dehydrogenase, malate dehydrogenase, and various isoforms of human LDH (LDH-A, LDH-B, and LDH-C), are similarly taken up and retained by cells undergoing apoptosis and necrosis. In contrast and as disclosed herein, this phenomenon is specific for dehydrogenase because glutathione S-transferase (GST), a non-dehydrogenase enzyme of nearly identical molecular weight to LDH, is not taken up and retained by dying cells, whereas GST-LDH conjugates are taken up and retained by dying cells.

Significantly, as described herein, LDH probes do not merely function as vital dyes by passive diffusion into dead cells after loss of membrane integrity. First, LDH probes stain cells in early apoptosis (i.e., Annexin V positive, vital dye negative). Second, LDH probes do not freely diffuse out of cells with extensive washing.

Dehydrogenases are ubiquitous, highly conserved enzymes that catalyze the transfer of a proton and a pair of electrons from a donor molecule to an acceptor molecule, thereby oxidizing the donor and reducing the acceptor. These enzymes typically use NAD/NADP or a flavin coenzyme such as FAD or FMN as the receptor. Dehydrogenases specifically include, but are not limited to, lactate dehydrogenase, alcohol dehydrogenase, aldehyde dehydrogenase, and malate dehydrogenase. Additional representative dehydrogenases are listed in Table 1.

TABLE 1

Representative List of Dehydrogenases

1-Pyrroline-5-carboxylate dehydrogenase
2-Oxoaldehyde dehydrogenase
2-Oxoisovalerate dehydrogenase
3-Dehydro-L-gulonate 2-dehydrogenase
3-Hydroxyacyl-CoA dehydrogenase
3-Hydroxybutyrate dehydrogenase
3-Hydroxybutyryl-CoA dehydrogenase
3-Hydroxyisobutyrate dehydrogenase
3-Isopropylmalate dehydrogenase
Acetaldehyde dehydrogenase
Acyl-CoA dehydrogenase
Alanine dehydrogenase
Alcohol dehydrogenase
Aldehyde dehydrogenase
Alpha-ketoglutarate dehydrogenase
Aminomuconate-semialdehyde dehydrogenase
Aspartate-semialdehyde dehydrogenase
Benzaldehyde dehydrogenase
Betaine-aldehyde dehydrogenase
Butyryl-CoA dehydrogenase
Choline dehydrogenase
Dihydrolipoamide dehydrogenase
Dihydrouracil dehydrogenase
Dimethylglycine dehydrogenase
Formyltetrahydrofolate dehydrogenase
Glucose-6-phosphate dehydrogenase
Glutamate dehydrogenase
Glutamate-5-semialdehyde dehydrogenase
Glutaryl-CoA dehydrogenase
Glyceraldehyde-3-phosphate dehydrogenase
Glycerate dehydrogenase
Glycerol-3-phosphate dehydrogenase
Glycine dehydrogenase
Glycolaldehyde dehydrogenase
Histidinol dehydrogenase
Homoserine dehydrogenase
Hypotaurine dehydrogenase
IMP-dehydrogenase
Isocitrate dehydrogenase
Isovaleryl-CoA dehydrogenase
Lactate dehydrogenase
1-Aminoadipate-semialdehyde dehydrogenase
Leucine dehydrogenase
1-Gulonate dehydrogenase
1-Iditol dehydrogenase
Malate dehydrogenase
Malonate semialdehyde dehydrogenase
Methylmalonate-semialdehyde dehydrogenase
NADH dehydrogenase
Oxoglutarate dehydrogenase
Phosphogluconate dehydrogenase
Phosphoglycerate dehydrogenase TABLE 1-continued Representative List of Dehydrogenases Proline dehydrogenase
Pyruvate dehydrogenase
Retinal dehydrogenase
Retinol dehydrogenase
Ribitol dehydrogenase
Saccharopine dehydrogenase
Sarcosine dehydrogenase
Serine dehydrogenase
Shikimate dehydrogenase
Sorbitol dehydrogenase
Succinate dehydrogenase
Succinate-semialdehyde dehydrogenase
Tryptophan dehydrogenase
UDP-glucose dehydrogenase
UDP-N-acetylmuramate dehydrogenase
Valine dehydrogenase
Xanthine dehydrogenase These and other dehydrogenases, including their nucleotide and amino acid sequences, have been extensively studied and are well known in the art. In addition, preparations of these and other dehydrogenases, including various individual isoenzymes (isozymes), are available from a number of commercial sources, including, for example, Sigma-Aldrich, St. Louis, Mo.

Thus, these and other dehydrogenases, which include full-length counterparts, as well as fragments thereof, are embraced by the invention, to the extent that they retain the ability to be taken up by dying cells (e.g., apoptotic and necrotic cells) as described herein. Also embraced by the invention are conjugates and fusion proteins comprising full-length dehydrogenases or fragments of dehydrogenases to the extent that they retain the ability to be taken up by dying cells (e.g., apoptotic and necrotic cells) as described herein.

In one embodiment the dehydrogenase used in the invention is a human dehydrogenase. In humans there are at least as many as 205 dehydrogenase genes.

In one embodiment the dehydrogenase used in the invention is a lactate dehydrogenase (LDH). In one embodiment the dehydrogenase used in the invention is a mammalian LDH. The term "lactate dehydrogenase" or, equivalently, "LDH" as used herein encompasses the A, B and C forms of LDH as well as cytoplasmic, mitochondrial, or otherwise compartmentalized forms of the enzyme (e.g., in the endoplasmic reticulum or membrane-bound within the cytoplasm). The term "lactate dehydrogenase" or, equivalently, "LDH" in one embodiment also includes modified (e.g., mutated, truncated) forms of LDH that retain the ability to be taken up by dying cells (e.g., apoptotic and necrotic cells) in accordance with the invention.

Moreover, the term "lactate dehydrogenase" or, equivalently, "LDH" refers to a single subunit (e.g., LDH-A, LDH-B, or LDH-C) or a multimer of subunits (e.g., the mature tetrameric enzyme), or both, depending upon the context.

Mammalian LDH is a tetrameric enzyme composed of A, B, and/or C subunits. There are five isozymes of LDH enzyme resulting from the assembly of homotetramers (AAAA ($A_4$) or BBBB ($B_4$)) or heterotetramers (ABBB, AABB, AAAB) of the A and B isoforms. The B isoform predominates in heart muscle and facilitates the aerobic oxidation of pyruvate. The A subunit predominates in skeletal muscle and liver and is primarily implicated with anaerobic metabolism and pyruvate reduction to lactate. To date, only the A form has been identified in islet β-cells. Another LDH isoform, LDH-C, is a homotetramer of C ($C_4$) and has been identified in spermatozoa.

LDH shares structural similarities with other NAD-binding enzymes. The polypeptide chain of each subunit folds into two clearly separated domains. The two domains have different functions and appear to each comprise a separate module. One of the domains (domain 1) binds to the coenzyme, NAD/NADH, and the second (domain 2) binds the substrate (e.g., pyruvate or lactate) and also provides the amino acid residues that are involved in catalysis. The coenzyme-binding domain is in the amino-terminal portion of the polypeptide. The active site of the enzyme is the cleft or "vacuole" that is formed between the two domains. The coenzyme-binding site on the one domain and the substrate-binding site on the other are oriented so that the C4 position of the nicotinamide ring is in close proximity to the hydrogen atom to be transferred between the substrate and coenzyme.

In one embodiment the dehydrogenase used in the invention is a human LDH. In mammals, lactate dehydrogenase A (LDH-A) (muscle), B (heart), and C (testis) polypeptide chains are encoded by individual genes. Holmes RS (1972) *FEBS Lett* 28:51-55; Li S S et al. (1983) *J Biol Chem* 258: 7029-7031; Takeno T et al. (1989) *Biochem J* 257:921-924. Human LDH-A and LDH-C genes are on chromosome 11 and human LDH-B gene is on chromosome 12. The expression of these three LDH genes is developmentally regulated and tissue-specific. Markert C L et al. (1975) *Science* 189: 102-114. A cDNA sequence for human LDH-A is available as GenBank Accession No. NM_005566; the corresponding amino acid sequence is available as GenBank Accession No. NP_005557. A cDNA sequence for human LDH-B is available as GenBank Accession No. NM_002300; the corresponding amino acid sequence is available as GenBank Accession No. NP_002291. A cDNA sequence for human LDH-C is available as GenBank Accession No. NM_002301; the corresponding amino acid sequence is available as GenBank Accession No. NP_002292.

In one embodiment the dehydrogenase used in the invention is an alcohol dehydrogenase (ADH). In one embodiment the dehydrogenase used in the invention is a mammalian ADH. In one embodiment the dehydrogenase used in the invention is a human ADH. The term "alcohol dehydrogenase" or, equivalently, "ADH" in one embodiment also includes modified (e.g., mutated, truncated) forms of ADH that retain the ability to be taken up by dying cells (e.g., apoptotic and necrotic cells) in accordance with the invention. Human ADH is a homodimer or heterodimer composed of $\alpha$, $\beta$, and/or $\gamma$ polypeptides encoded by separate gene loci, $ADH_1$, $ADH_2$, and $ADH_3$. A cDNA sequence for human ADH $\alpha$ is available as GenBank Accession No. NM_000667; the corresponding amino acid sequence is available as GenBank Accession No. NP_000658. A cDNA sequence for human ADH $\beta$ is available as GenBank Accession No. NM_000668; the corresponding amino acid sequence is available as GenBank Accession No. NP_000659. A cDNA sequence for human ADH $\gamma$ is available as GenBank Accession No. NM_000669; the corresponding amino acid sequence is available as GenBank Accession No. NP_000660.

In one embodiment the dehydrogenase used in the invention is an aldehyde dehydrogenase (ALDH). In one embodiment the dehydrogenase used in the invention is a mammalian ALDH. In one embodiment the dehydrogenase used in the invention is a human ALDH. The term "aldehyde dehydrogenase" or, equivalently, "ALDH" in one embodiment also includes modified (e.g., mutated, truncated) forms of ALDH that retain the ability to be taken up by dying cells (e.g., apoptotic and necrotic cells) in accordance with the invention. Aldehyde dehydrogenases are a group of enzymes that catalyze the oxidation (dehydrogenation) of aldehydes. Mitochondrial Aldehyde Dehydrogenase is a polymorphic enzyme responsible for the oxidation of aldehydes to carboxylic acids, which leave the liver and are metabolized by the body's muscle and heart. There are three different classes of these enzymes in mammals: class 1 (low $K_m$, cytosolic), class 2 (low $K_m$, mitochondrial), and class 3 (high $K_m$, such as those expressed in tumors, stomach and cornea). In all three classes constitutive and inducible forms exist. ALDH1 and ALDH2 are the most important enzymes for aldehyde oxidation, and both are tetrameric enzymes composed of ~54 kDa subunits. These enzymes are found in many tissues of the body, but are at the highest concentration in the liver (See: Crabb D W, Matsumoto M, Chang D, You M (2004). "Overview of the role of alcohol dehydrogenase and aldehyde dehydrogenase and their variants in the genesis of alcohol-related pathology". *The Proceedings of the Nutrition Society* 63(1): 49-63).

In one embodiment the dehydrogenase used in the invention is a malate dehydrogenase (MDH). In one embodiment the dehydrogenase used in the invention is a mammalian MDH. In one embodiment the dehydrogenase used in the invention is a human MDH. The term "maltate dehydrogenase" or, equivalently, "MDH" in one embodiment also includes modified (e.g., mutated, truncated) forms of MDH that retain the ability to be taken up by dying cells (e.g., apoptotic and necrotic cells) in accordance with the invention. Malate dehydrogenase (EC 1.1.1.37) is an enzyme in the citric acid cycle that catalyzes the conversion of malate into oxaloacetate (using $NAD^+$) and vice versa. Malate dehydrogenase is also involved in gluconeogenesis, the synthesis of glucose from smaller molecules. Pyruvate in the mitochondria is acted upon by pyruvate carboxylase to form oxaloacetate, a citric acid cycle intermediate. In order to get the oxaloacetate out of the mitochondria, mitochondrial malate dehydrogenase reduces it to malate, which then traverses the inner mitochondrial membrane. Once in the cytosol, the malate is oxidized back to oxaloacetate by cytosolic malate dehydrogenase. Finally, phosphoenol-pyruvate carboxy kinase converts oxaloacetate to phosphoenol pyruvate. Banaszak L J et al. In: Boyer P D (Ed.), *The Enzymes*, 3rd ed., vol. 11, Academic Press, New York, 1975, p. 369-396. A cDNA sequence for human cytoplasmic MDH is available as GenBank Accession No. NM_005917; the corresponding amino acid sequence is available as GenBank Accession No. NP_005908.

In some embodiments, any of the dehydrogenases (e.g., LDH, ADH, ALDH and MDH) suitable for use according to the invention may be a full-length dehydrogenase or a truncated counterpart (e.g., fragments) thereof.

The structure-activity relationship of dehydrogenase probes comprising varied fragments or length and their ability to detect apoptotic cells can be established by techniques known in the art. Understanding the structural requirements for binding of dehydrogenase probes to dead cells is important for subsequent optimization of the particular probes for in vivo use. Since a number of dehydrogenases similarly bind to apoptotic cells (See Examples), the structural determinants of binding are likely to be contained within regions of conserved sequence or structure. Thus, systematic mutagenesis and ectopic fusions may be used to identify the structural elements that are necessary and those that are sufficient for the binding of the particular dehydrogenase probe of interest to apoptotic cells.

For example, as presented in the Examples herein, all hLDH subunits appropriately bind to apoptotic cells, even when fused to GST. As such, GST-hLDHA can be systematically mutated to identify the regions that are necessary for binding to apoptotic cells. Then, the domain(s) identified to as necessary can be fused to ectopic proteins, followed by systematic truncation, to determine which domains are sufficient to confer binding to apoptotic cells. Finally, protein size limits may be determined for appropriate detection of apoptotic cells, since this may be a critical determinant of in vivo pharmacokinetics.

In some cases, the protein domain structure of a dehydrogenase of interest may be deduced from the amino acid sequence of the protein using appropriate programs that are known in the art, such as the InterPro database, which may provide guidance for designing a truncated dehydrogenase (e.g., a fragment) for use according to the invention. To demonstrate, hLDHA is analyzed as an example. The InterPro database identifies the following conserved domains in the hLDH amino acid sequence, which may be deleted by site-directed mutagenesis:

| Amino acids | Domain Name |
| --- | --- |
| 21-161 | NAD binding domain |
| 163-329 | Alpha/beta C-terminal domain |
| 22-46 | LDH signature 1 |
| 47-71 | LDH signature 2, tetramerization interface |
| 134-154 | LDH signature 3 |
| 158-176 | LDH signature 4, tetramerization interface |
| 188-201 | LDH signature 5 and active site |
| 1-35 | Prokaryotic lipoprotein homology |

Similar strategies may be used to construct any other dehydrogenase probes comprising is truncated (e.g., fragment) dehydrogenase proteins. Accordingly, to identify the domains of a dehydrogenase probe necessary for detecting dying cells, an expression plasmid encoding the dehydrogenase or fragment thereof (e.g., hLDHA, B, and C) is used, and a truncated form of a probe may be designed based initially on evolutionarily-conserved domains. In some embodiments, the expression plasmid is a bacterial expression vector, examples of which are provided elsewhere herein. A number of suitable expression systems are available and known in the art, including a GST-based system.

In some embodiments, such a construct encoding a fragment or a mutant of a dehydrogenase to be evaluated can be expressed in bacteria or other suitable expression host system and purified as previously described (Kung, A. L. et al., Nat Med, 2000. 6: 1335-40; Freedman, S. J. et al., Proc Natl Acad Sci USA, 2002. 99: 5367-72). In some embodiments, BL21 (DE3) bacteria are transformed with the plasmids, liquid cultures are induced to express the fusion proteins using IPTG, and GST-fusion proteins are affinity-purified on glutathione Sepharose 4B (Amersham Pharmacia). After elution, recombinant GST-fusion proteins are analyzed by SDS-PAGE and Coomassie staining, and total protein concentration is quantified by Bradford Assay (BioRad).

Recombinant proteins are then conjugated to a suitable detectable label, for example, Cy5.5, as shown in the Examples herein. Protocols for generating fusion proteins are known in the art. An exemplary condition for producing a GST fusion protein of a dehydrogenase suitable for the instant disclosure is as follows: 30 μg of recombinant GST-hLDH is mixed with 0.1 M bicarbonate (pH 8.0) and reacted with 2 μL of Cy5.5 N-hydroxysuccinimide ester (Amersham Pharmacia) dissolved in anhydrous DMSO (1 mg Cy5.5-NHS in 12 μL DMSO). The labeling ratio is 2:1 (mol Cy5.5: GST-LDHA), which prevents quenching that can occur at high labeling ratios. The mass of each probe is adjusted based on the calculated molecular weight to maintain this 2:1 labeling ratio. The reaction mixture is incubated for 1 hr at room temperature and 4 hrs at 4° C. Covalently conjugated Cy5.5-hLDHB-derived probes are separated from non-reacted dye by Biogel P6 spin columns (BioRad).

To test the probes, suspension cells are useful, such as RS(4;11) and THP-1 cells treated with a HDAC inhibitor (LAQ824, 50 nM) to induce apoptosis, Probes may be added directly to the growth media to a suitable final concentration, e.g., 0.5 μM, since staining with LDH is not diminished by FBS and supra-physiological calcium is not required (See Examples). In all cases, cells can be simultaneously stained with FITC-GST-hLDHA. Cells may be analyzed using multi-color FACS. The ability of mutants (Cy5.5 conjugates) to be taken up by apoptotic cells can be compared to staining by full-length hLDHA (FITC conjugate) in the same sample.

In some cases, any region that is found to be necessary for a dehydrogenase binding of apoptotic cells may be more finely mapped using scanning linker substitution. An unlimited example of such a linker includes Asn-Ala-Ala-Ile-Arg-Ser (NAAIRS) (SEQ ID NO:1) which has been described (Kung, A. L. et al., Nat Med, 2000. 6: 1335-40). Site-directed mutagenesis can be used to create a series of mutants in which the native sequence is substituted with the 6 amino acid sequence Asn-Ala-Ala-Ile-Arg-Ser (NAAIRS) (SEQ ID NO: 1) Since this sequence can be incorporated into an alpha-helix or a beta-sheet (Wilson, I. A. et al., Proc Natl Acad Sci USA, 1985. 82: 5255-9), NAAIRS-substitution is less likely to globally disrupt secondary structure by comparison to either deletion or poly-Alanine substitution. The NAAIRS mutants can be made in the context of a full-length dehydrogenase of interest. Applying to the above example, if deletion of the prokaryotic lipoprotein homology region (amino acid residues 1-35) above disrupts staining, a series of NAAIRS substitution mutants may be created, in which amino acid residues 2-7, amino acid residues 8-13, amino acid residues 14-19, amino acid residues 20-25, amino acid residues 26-31, and amino acid residues 32-37 are mutated in the context of full-length GST-hLDHA. The mutants can be then purified, labeled with Cy5.5, and staining can be compared to native FITC-GST-hLDHA as described above.

Preferably, an extra stretch of amino acid residues (e.g., ~10-30 residues) is added on each side of regions (e.g., domains) of a dehydrogenase determined to be important for binding apoptotic cells. For example, if the enzymatic active site (amino acid residues 188-201) is found to be necessary for staining, amino acid residues ~168-221 are subcloned to create a bacterial expression plasmid. Recombinant protein can then be produced and labeled as described above, and the binding characteristics can be compared to the full-length counterpart using FACS as described above.

In certain embodiments, it is desirable to define size limits for dehydrogenase probes as used according to the invention. The serum half-life of human LDH is between 50-100 hours (Smit, M. J. et al. Clin Chem, 1988. 34: 2475-80), and it is likely that in vivo imaging characteristics will be improved by increasing the clearance of the probe (Batra, S. K. et al. Curr Opin Biotechnol, 2002. 13: 603-8.). Therefore, once the above studies define the regions that are necessary and those that are sufficient for binding to dying cells, deletion mutants of a suitable dehydrogenase (e.g., fragments) may be designed that decreases the molecular weight, for instance, from 38 kDa, to 30 kDa (hLDHA[30k]) and 20 kDa (hLDHA [20k]) in the case of hLDHA. The resulting recombinant proteins can be initially produced, for example, as GST-fusion proteins, but in some cases, instead of eluting the fusion protein with excess glutathione, the dehydrogenase polypeptides may be liberated from the bound GST moiety by cleavage with an appropriate protease, such as PreScission protease (Amersham Pharmacia). Polypeptides can then be labeled as described herein. To test the resulting dehydrogenase probes, any appropriate in vitro assay may be employed. For example, apoptosis can be induced in THP-1 cells by treatment with HDAC inhibitor (LAQ824, 50 nM, 18 hrs), and cells are dual-stained with Annexin V-FITC and each dehydrogenase probe (e.g., hLDHA-Cy5.5, hLDHA[30k]-Cy5.5, and hLDHA[20k]-Cy5.5). Dual color FACS can be used to compare the three hLDHA probes for their ability to bind to Annexin V-positive apoptotic cells.

Certain aspects the invention also relate to conjugates of a dehydrogenase linked to a detectable label. The term "conjugate" as used herein is a molecule or complex formed by linking a molecule to at least one other molecule or other moiety. In one embodiment the conjugate is stable under physiological conditions, i.e., the linked components remain linked together under physiological conditions. The linkage can be any suitable chemical or physicochemical linkage, including a covalent bond and a noncovalent bond. In one embodiment the conjugate is a recombinant fusion protein. The linkage between any two components of the conjugate can be direct, i.e., without a linker moiety, or it can be indirect, i.e., it can include a linker moiety connecting the two components. In one embodiment the linkage involves a biotin-streptavidin interaction. In one embodiment the dehydrogenase is linked to a detectable label via an enzymatically cleavable linkage.

The dehydrogenase is linked to a detectable label. As used herein, a "detectable label" is a molecular or atomic tag or marker that generates or can be induced to generate an optical or other signal or product that can be detected visually or by using a suitable detector. Detectable labels are well known in the art and include, without limitation, fluorescent labels, radioisotopes, nanoparticles, chromophores, dyes, enzymes, and contrast agents.

Fluorescent labels commonly used include Alexa, cyanine such as Cy5™ and Cy5.5™, and indocyanine, and fluorescein isothiocyanate (FITC), but they are not so limited. In general such fluorescent labels and their derivatives can react with carboxyl, amino, or sulfhydryl functional groups of the dehydrogenase. Fluorescent labels useful in the practice of the invention can include, also without limitation, 1,5 IAEDANS; 1,8-ANS; 4-Methylumbelliferone; 5-carboxy-2, 7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange+DNA; Acridine Orange+RNA; Acridine Orange, both DNA & RNA; Acridine Red; Acridine Yellow; Acriflavin; Acriflavin Feulgen SITSA; Aequorin (Photoprotein); Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminocoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC=Ratio Dye, $Zn^{2+}$; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisamninophenyloxadiazole); BCECF (high pH); BCECF (low pH); Berberine Sulphate; Beta Lactamase; BFP blue shifted GFP (Y66H); Blue Fluorescent Protein; BFP/GFP FRET Bimane; Bisbenzamnide; Bisbenzimide (Hoechst); bis-BTC=Ratio Dye, $Zn^{2+}$; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC-Ratio Dye $Ca^{2+}$; BTC-5N-atio Dye, $Zn^{2+}$; Calcein; Calcein Blue; Calcium Crimson™; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow 399; Catecholamine; CCF2 (GeneBlazer); CFDA; CFP—Cyan Fluorescent Protein; CFP/YFP; FRET; Chlorophyll; Chromomycin A; Chromomycin A; CL-NERF (Ratio Dye, pH); CMFDA; Coelenterazine; Coelenterazine cp ($Ca^{2+}$ Dye); Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); CyQuant Cell Proliferation Assay; Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiIC18(7)); DM-NERF (high pH); DNP; Dopamine; DsRed; Red fluorescent protein; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FIF (Formaldehyde Induced Fluorescence); FITC; FITC Antibody; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2, high calcium; Fura-2, low calcium; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP), GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DiR); Intrawhite Cf; JC-1; JO-JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; LIVE/DEAD Kit Animal Cells, Calcein/Ethidium homodimer; LOLO-1;

LO-PRO-1; Lucifer Yellow; Lyso Tracker Blue; Lyso Tracker Blue-White; Lyso Tracker Green; Lyso Tracker Red; Lyso Tracker Yellow; LysoSensor Blue, LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin E8G; Oregon Green; Oregon Green 488-X; Oregon Green™; Oregon Green™ 488; Oregon Green™ 500; Oregon Greene™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodide (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYT; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodamineIsoThioCyanate); True Blue; TruRed; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO-3; YOYO-1; and YOYO-3.

In one embodiment the fluorescent label is a fluorescent protein. The fluorescent protein can be linked to a dehydrogenase by conventional chemical methods, or it can be expressed together with the dehydrogenase as a fusion protein. A wide variety of fluorescent proteins are available in a broad range of the light spectrum, including red, orange, yellow-green, green, cyan and UV-excitable green. Non-limiting examples of fluorescent proteins that can be used as labels include mPlum, mCherry, tdTomato, mStrawberry, J-Red, DsRed-monomer, mOrange, mKO, mCitrine, Venus, YPet, EYFP, Emerald, EGFP, CyPet, mCFPm, Cerulean, T-Sapphire, Citrine, mYFP, ECFP, mCFP, EBFP, AceGFP (available from Evrogen), AcGFP1 (available from Clontech), AmCyan1 (available from Clontech), AQ143 (available from Lukyanov), AsRed2 (available from Clontech), Azami-Green/mAG (available from MBL Intl.), cOFP (available from Stratagene), CopGFP (available from Evrogen), dimer2, tdimer2(12) (developed by Tsien), DsRed/DsRed2/DsRed-Express (available from Clontech), EBFP (sold by Clontech; no longer commercially available), eqFP611 (developed by Weidenmann), HcRed1 (available from Clontech), HcRed-tandem (available from Evrogen), Kaede (available from MBL Intl.), mBanana (developed by Tsien), mHoneydew (developed by Tsien), MiCy (available from MBL Intl.), mRaspberry (developed by Tsien), mRFP1 (developed by Tsien), mTangerine (developed by Tsien), mYFP (developed by Tsien), PhiYFP (available from Evrogen), Renilla GFPs (various sources), TurboGFP (available from Evrogen) and ZsYellow1 (available from Clontech). In one embodiment the fluorescent label is a far-red fluorescent protein suitable for use in whole-body imaging, such as Katushka and derivatives thereof. Shcherbo D et al. (2007) *Nat Methods* 4:741-6. For a review of fluorescent proteins, see Shaner N C et al. (2005) *Nat Methods* 2:905-909.

As used herein, a "chromophore" is a chemical group that produces color in a compound. A dye is a colored compound, such as a stain, that includes a chromophore.

There are many effective biological stains available in the art. Different stains react or concentrate in different parts of a cell or tissue, and these properties are used to advantage to reveal specific parts or areas. Generally, these dyes may be used with fixed cells and tissues, and some are particularly suitable for use with living organisms ("Vital dyes"). Non-limiting examples of biological stains that are commonly used include: Bismarck brown, Carmine, Coomassie blue, Crystal violet, DAPI, Eosin, Ethidium bromide, Fuchsin, Haematoxylin, Hoechst stains, Iodine, Malachite green, Methyl green, Methylene blue, Neutral red, Nile blue, Nile red, Osmium tetroxide, Rhodamine, and Safranin.

Radioisotopes useful in the invention are well known in the art and can include $^3$H, $^{11}$C, $^{18}$F, $^{35}$S, $^{64}$Cu, $^{67}$Ga, $^{68}$Ga, $^{99m}$Tc, $^{111}$In, $^{123}$I, $^{124}$I, $^{125}$I, and $^{131}$I. Attachment of any gamma emitting radioactive materials, e.g., $^{99m}$Tc and $^{111}$In, which can react with carboxyl, amino, or sulfhydryl groups of dehydrogenase, is suitable for use in detection methods using gamma scintigraphy. Attachment of radioactive $^{11}$C, $^{18}$F, $^{64}$Cu, $^{67}$Ga, $^{68}$Ga, $^{124}$I, and $^{131}$I compounds which can react with carboxyl, amino, or sulfhydryl groups of dehydrogenase, is suitable for use in detection methods using PET/SPECT imaging.

As used herein, a "nanoparticle" is a particle about 1 nm ($10^{-9}$ m) to 250 nm in diameter that is capable of being taken up by cells. Nanoparticles specifically include but are not limited to quantum dots, gold nanoparticles, and superparamagnetic particles. Quantum dots, which are also known as fluorescent semiconductor crystals or qdots, have recently been described as highly versatile agents for use in in vivo imaging, tumor targeting, and diagnostics. See, for example, Michalet X et al. (2005) *Science* 307:538-544. Nanoparticles, including quantum dots and their derivatives, either alone or in combination with other agents that can react with carboxyl, amino, or sulfhydryl groups of dehydrogenase, are suitable for use in detection methods using optical imaging.

Additional detectable labels useful in the invention include T1 and T2 contrast agents useful in magnetic resonance imaging (MRI). These can include chelates of gadolinium which can react with carboxyl, amino, or sulfhydryl groups of dehydrogenase, as well as any superparamagnetic nanoparticles such as iron oxide and cobalt oxide which can react with carboxyl, amino, or sulfhydryl groups of dehydrogenase.

A detectable label in one embodiment is an enzyme. The enzyme can act on an appropriate substrate to result in production of a detectable dye. Examples of enzymes useful in the invention include, without limitation, alkaline phosphatase and horseradish peroxidase. Alternatively or in addition, the enzyme can be, for example, luciferase. The enzyme can be linked to a dehydrogenase by conventional chemical methods, or it can be expressed together with the dehydrogenase as a fusion protein.

Yet further additional detectable labels useful in the invention include other contrast agents, particularly radiocontrast agents such as barium or other metals, provided in a form which can react with carboxyl, amino, or sulfhydryl groups of dehydrogenase.

Of course detectable labels also include any combination of the above-described detectable labels.

In one embodiment the detectable label excludes an immunoglobulin or fragment thereof which is capable of binding to the dehydrogenase. In a particular embodiment, the detectable label excludes an immunoglobulin or fragment thereof which is capable of binding to lactate dehydrogenase.

Although fluorescent conjugates are suitable for in vitro assays (e.g., FACS, microscopy), there are often limitations to their use in vivo, even in preclinical models. As such, it may be desirable to develop radionuclide-labeled dehydrogenase probes to assess biodistribution and for so subsequent in vivo imaging. Since many of the dehydrogenases useful for the invention, e.g., hLDHA, are moderate-sized proteins, radioiodination should be a facile means of generating a radioligand. As for hLDHA, for example, there are eight tyrosine residues in the protein.

An exemplary protocol for radiosynthesis of a dehydrogenase probe is as follows. Full-length and/or truncated dehydrogenase of interest, e.g., hLDHA, is radioiodinated with $^{125}$I, and its binding function can be first verified in dying cells in vitro. Typically, $^{125}$I-hLDHA probes are tested in vitro, comparing no cells (control) to live and dead cells. For example, apoptotic HeLa cells can be generated by treating cells with camptothecin (10 µM, 18 hours). Either PBS (control), or $10^7$ live or dead cells in PBS are placed in microfuge tubes, and 100,000 cpm of each probe added to each tube (full-length hLDHA and 5 derivatives). After incubating for 1 hr, tubes are centrifuged, and the activity in the supernatant determined by gamma counter. The bound fraction will be determined by comparing the activity in cell-containing tubes to that in the PBS-only tubes. Probes with proper targeting will also be characterized by significantly increased binding to apoptotic cells by comparison to live cells.

To determine biodistribution of probes in vivo, probes can then be injected into mice followed by timed collection and gamma-counting of tissue to determine biodistribution to evaluate the pharmacokinetics of the radio-labeled dehydrogenase in vivo. For example, male NCr nude mice (8 wks) are injected via tail vein with 10-20 µCi of the $^{125}$I-hLDHA probes. Mice are sacrificed at intervals, e.g., 0, 1, 2, 4, 8, 16, 24, 48, and 72 hrs after injection. Blood, urine, liver, stomach, bowel, bowel content, thyroid, kidney, spleen, lungs, myocardium, and muscle are harvested, weighed, and radioactivity determined using a gamma counter. Values are corrected for decay, and data are expressed as fraction of injected dose per gram of tissue. Clearance can be calculated using a multi-exponential fit. It should be noted that truncated forms of dehydrogenases (e.g., hLDHA[20k]) may have more rapid clearance in vivo as compared to their fill-length counterparts. In some cases, it is also possible to assess alternative probes in which a dehydrogenase is destabilized by clinically relevant point mutations (Sudo, K. et al., *Hum Genet,* 1992. 89: 158-62).

The dehydrogenase probes described herein are useful for detecting cell death in a subject, and methods for such use are also provided. A number of in vivo models suitable for evaluating dehydrogenase probes are available. Some of these in vivo models are provided in the Examples.

In some embodiments, in vivo imaging of fulminant hepatic failure may be carried out. Hepatocyte apoptosis may be induced with the use of an anti-Fas antibody, which is known in the art. For example, in a typical experiment, NCr nude mice may be injected with either the anti-Fas antibody (Jo2, Pharmingen) or an isotype-matched control antibody. The synchronous induction of apoptosis in hepatocytes in this model system is well established (Chang, B. et al., *Arch Biochem Biophys,* 2003. 411: 63-72; Feng, G. and N. Kaplowitz, *J Clin Invest,* 2000. 105: 329-39; Nishimura, Y. et al., *Int Immunol,* 1997. 9: 307-16; Ogasawara, J. et al., *Nature,* 1993. 364: 806-9). As such, 300-500 µCi of the $^{124}$I-hLDHA probe may be injected ~2 hours later. Animals undergo micro-PET/CT imaging, which is known in the art. Briefly, animals undergo imaging immediately after injection and at 3, 6, 9, 12, 24, 36, and 48 hrs after probe injection. Animals are then sacrificed after the 48 hr imaging point. Urine, stomach, bowel, bowel content, thyroid, liver, kidneys, lung, myocardium, and spleen will be harvested, weighed, and radioactivity determined by gamma counter. Activity will be corrected for decay, and expressed as fraction of injected dose per gram of tissue. Iterative PET image reconstruction and analysis can be then performed.

As illustrated in the Examples using fluorescent LDH probes, radio-labeled dehydrogenase probes can similarly be used to specifically bind to dead cells in vitro. As presented in FIG. 8, the near infrared LDH probes suggest that the native (e.g., full-length) $^{124}$I-hLDHA probe may be well suited for use in the fulminant hepatic failure model. It should be taken into account that, in some cases, full-length dehydrogenase probes, such as native LDH, are anticipated to have prolonged elimination half-life for the probe, depending on the half-life of the protein in serum. For instance, the serum half-life of human LDH is between 50-100 hours (Smit, M. J. et al., *Clin Chem,* 1988. 34: 2475-80). This may result in increased background due to prolonged circulation of the probe in the blood compartment. Kinetic analysis of the imaging studies and the biodistribution studies as described herein may help precisely determine distribution and elimination kinetics for the probe, which is helpful for the optimization of particular probes for clinical applications.

Optimization of dehydrogenase-based probes for in vivo imaging may be carried out using techniques that are familiar in the art. As described herein, radioiodinated dehydrogenase probes, such as hLDHA probes, as well as truncated derivatives that retain the ability to be taken up by dying cells, but with varying clearance in vivo, may be optimized for suitable application. For example, one of ordinary skill in the art can readily assess the ability of these probes to image apoptosis in vivo, using a fulminant hepatic failure model, an oncogene withdrawal model, and a cancer treatment model, etc. To increase sensitivity and improve quantification, the positron-emitter $^{124}$I for Positron Emission Tomography (PET) imaging may be employed.

Non-limiting examples of suitable optimization models include a model in which fulminant hepatocyte apoptosis is induced, a model with inducible expression of the Ras oncogene to induce apoptosis by withdrawal of Ras expression in established tumors (Tang, Y. et al., *Cancer Res*, 2005. 65: 8324-30), and apoptosis induced by chemotherapy treatment of established orthotopic breast tumors. In any of these cases, [124]I-hLDHA and other derivative probes may be assessed by using micro-PET/CT imaging, followed by histological validation.

Micro-PET/CT imaging is known in the art, In some embodiments, to facilitate histological validation, an epitope (e.g., a tag) may be added to the recombinant polypeptide. In some cases, a 9-amino acid hemagglutinin epitope (HA tag) YPYDVPDYA (SEQ ID NO:2) is added to the recombinant polypeptides. However, any other suitable tags may be used. In some embodiments, Na $^{124}$I may be used for radioiodination. Each probe may be evaluated by serially imaging control animals and experimental animals. With the fulminant hepatic failure model, animals injected with the anti-Fas antibody develop hepatic failure, so appropriate group sizes for an experiment may be ~4 control and ~4 treated with anti-Fas antibody. For the inducible Ras model and for the breast cancer cell model, a greater number of animals may be implanted, e.g., ~20 mice, with tumor cells to be able to select out ~8 mice with closely matched tumor size for the two treatment arms (n=4/group).

The PET/CT imaging technology is known in the art, and the skilled artisan can readily adapt a suitable system, such as a Siemens Inveon preclinical multimodality system. This scanner has been previously shown to provide high resolution and high sensitivity small animal molecular imaging (Visser, E. P. et al., *J Nucl Med*, 2009. 50: 139-47). The Inveon CT component provides high resolution anatomical images with intrinsic image co-registration that can be used for definition of regions-of-interest (ROI), and PET attenuation and scatter correction.

Iterative PET image reconstruction will be performed including corrections for detector efficiency, random coincidences, photon attenuation, and radioactive decay to produce images. In addition to the absolute radioactivity concentration, the standardized uptake value (SUV) (Thie J. A., *J. Nucl Med*, 2004. 45(9): 1431-34) for all the ROIs may be calculated for comparisons with standard clinical measurements. The target/background ratios are also recorded as a function of time using surrounding normal tissues as background. The resulting curves may be used to evaluate image quality and the optimal time for imaging. Similarly, the organ and tumor TACs are used to characterize the biodistribution of the radiotracer as well as the radiation dosimetry profile.

In some cases, histological validation may be performed. After tissues undergo gamma counting, they may be fixed (for instance, for 24 hrs in 10% formalin). After decay of radioactivity is allowed, e.g., three weeks, the tissues are histologically processed and sectioned. Apoptosis may be assessed in the liver for the anti-Fas studies, and in tumors for the conditional Ras and chemotherapy studies. Apoptotic cells are identified by known methods, such as detection of activated caspase 3 or TUNEL assay. The dehydrogenase probes (e.g., HA-tagged hLDHA-derived probes) are detected. Nuclei may be counterstained with DAPI. As has been previously described, the percent apoptotic cells may be determined by immunofluorescence microscopy as the fraction of TUNEL or activated caspase 3 positive cells out of all nuclei counted (Rubin, J. B. et al., *Proc Natl Acad Sci USA*, 2003. 100: 13513-8). Results from these measurements may be used to validate the performance of the probes at the cellular level.

Certain aspects the invention relate to conjugates of a dehydrogenase linked to at least one therapeutic agent. As used herein, a "therapeutic agent" includes radionuclides, drugs, other small organic molecules (having molecular weight up to 1,500 Daltons), isolated toxins, polysaccharides, nucleic acids, inhibitory RNA; amino acids, peptides, polypeptides, and proteins including enzymes.

In one embodiment the therapeutic agent is an inhibitor of apoptosis. Apoptosis inhibitors include, without limitation, cyclocreatine, cyclocreatine phosphate, coenzyme Q10, L-carnitine, glutathione, α-lipoic acid, a caspase inhibiting peptide, and an inhibitor of apoptotic protein (IAP). Caspase inhibiting peptides include, but are not limited to Z-VAD, xVAD and Z-DEVD (SEQ ID NO:3). IAPs are a family of proteins characterized by a novel domain of ~70 amino acids termed the baculoviral IAP repeat (BIR), the name of which derives from the original discovery of these apoptosis suppressors in the genomes of baculoviruses by Lois Miller and her colleagues. Crook N E et al. (1993) *J Virol* 67:2168-2174; Birnbaum M J et al. (1994) *J Virol* 67:2521-2528. Up to three tandem copies of the BIR domain can occur within the known IAP family proteins of viruses and animal species. The conserved presence and spacing of cysteine and histidine residues observed within BIR domains ($CX_2CX_6WX_3DX_5HX_6C$) (SEQ ID NO:4) suggests that this structure represents a novel zinc-binding fold. Human IAPs include, without limitation, c-IAP-1, c-IAP-2, XIAP, and survivin. See, e.g., Deveraux Q L et al. (1999) *Genes Dev* 13:239-252; Sommer K W et al. (2004) *Oncogene* 22:4266-4280.

Additional inhibitors of apoptosis include BCL-2 family members, for example BCL-2 and BCL-$X_L$, as well as peptide derivatives thereof. Walensky L D et al. (2004) *Science* 305:1466-70; Walensky L D (2006) *Cell Death Differ* 13:1339-50.

Additional apoptosis inhibitors include, without limitation, Caspase Inhibitor I; InSolution™ Caspase Inhibitor I; Caspase Inhibitor I, Biotin Conjugate; Caspase Inhibitor II; Caspase Inhibitor II, Cell-Permeable; Caspase Inhibitor III; Caspase Inhibitor IV; Caspase Inhibitor VI; InSolution™ Caspase Inhibitor VI; Caspase Inhibitor VIII; Caspase Inhibitor X; Caspase Inhibitor, Negative Control; Caspase-1 Inhibitor I; Caspase-1 Inhibitor 1, Cell-Permeable; Caspase-1 Inhibitor II; Caspase-1 Inhibitor IV; Caspase-1 Inhibitor VI; Caspase-2 Inhibitor I; Caspase-2 Inhibitor II; Caspase-3 Inhibitor I; Caspase-3 Inhibitor I, Biotin Conjugate; Caspase-3 Inhibitor I, Cell-Permeable; InSolution™ Caspase-3 Inhibitor I, Cell-Permeable; Caspase-3 Inhibitor II; Caspase-3 Inhibitor II, Biotin Conjugate; InSolution™ Caspase-3 Inhibitor II; Caspase-3 Inhibitor III; Caspase-3 Inhibitor IV; Caspase-3 Inhibitor V; Caspase-3 Inhibitor VII; Caspase-3/7 Inhibitor II; Caspase-3/7 Inhibitor I; Caspase-4 Inhibitor I; Caspase-4 Inhibitor I, Cell-Permeable; Caspase-5 Inhibitor I; Caspase-6 Inhibitor I; Caspase-6 Inhibitor II, Cell-Permeable; Caspase-8 Inhibitor II; InSolution™ Caspase-8 Inhibitor II; Caspase-8 Inhibitor I, Cell-Permeable; Caspase-9 Inhibitor I; InSolution™ Caspase-9 Inhibitor I; Caspase-9 Inhibitor II, Cell-Permeable; Caspase-9 Inhibitor III; Caspase-1 Inhibitor II, Biotin Conjugate; Caspase-1 Inhibitor V; Caspase-13 Inhibitor I; Caspase-13 Inhibitor II; CrmA, Recombinant; Granzyme B Inhibitor I; Granzyme B Inhibitor II; Granzyme B Inhibitor IV; Group III Caspase Inhibitor I; Procaspase-3 Activator, PAC-1; and InSolution™ Q-VD-OPh, Non-O-methylated.

In one embodiment the therapeutic agent is an inhibitor or inducer of autophagy. Inducers of autophagy include, but are not limited to histone deacetylase (HDAC) inhibitors, tamoxifen, EB1089, anti-angiogenic agents, tyrosine kinase inhibitors, resveratrol, alkylating agents, arsenic trioxide, Akt inhibitors, HIV protease inhibitors, and mammalian target of rapamycin (mTOR) inhibitors. Inhibitors of autophagy include, but are not limited to chloroquine, hydroxychloroquine, omeprazole, BMS1, BMS2, BMS3, and BMS4, and microtubule disrupting agents. See Bialik S and Kimchi A (2008) *Adv Exp Med Biol* 615:177-200.

Conjugates of the invention can be isolated. As used herein, the term "isolated" means removed from the environment in which, and/or removed from other substances with which, the conjugate may be found in nature.

A substance can be isolated without being purified. Conjugates of the invention can be purified. As used herein, the term "purified" means substantially free of other substances. As used herein, in one embodiment the term "purified" means that a preparation of conjugate is, by weight, at least 80 percent conjugate. In one embodiment such a preparation is, by weight, at least 90 percent conjugate. In one embodiment such a preparation is, by weight, at least 95 percent conjugate. In one embodiment such a preparation is, by weight, at least 99 percent conjugate.

Conjugates of the invention, including but not limited to those just described above, can be used in the preparation of compositions that include such conjugates. Such compositions can be prepared by placing at least one conjugate of the invention in contact with at least one other moiety, such as a pharmaceutically acceptable carrier or solvent. The invention accordingly embraces both compositions which include at least one conjugate of the invention, as well as methods for making same. In one embodiment the composition is a pharmaceutical composition suitable for administration to a living subject.

Certain aspects the invention relate to a polynucleotide encoding a fusion protein of the invention. In one embodiment the polynucleotide of the invention is a polynucleotide encoding a dehydrogenase operably linked to a polynucleotide encoding a detectable label. In one embodiment the polynucleotide of the invention is a polynucleotide encoding a dehydrogenase operably linked to a polynucleotide encoding a therapeutic agent. As used herein, a "polynucleotide" refers to DNA and RNA molecules. A DNA polynucleotide of the invention can include genomic DNA sequence, complementary DNA (cDNA) sequence, or a combination of genomic sequence and cDNA sequence. The term "operably linked" as used herein means that the linked polynucleotide sequences are linked in a manner which allows for the expression of the resultant nucleotide sequence. For example, a polynucleotide encoding a dehydrogenase is operably linked to a polynucleotide encoding a fluorescent protein when the two component sequences are joined in such a manner as to generate a polynucleotide with a single continuous, correct translational reading frame for both polynucleotide components.

Examples of polynucleotide sequences encoding a dehydrogenase include those noted above in reference to human LDH, human ADH, human ALDH and human MDH.

Examples of polynucleotide sequences encoding a detectable label include sequences encoding fluorescent proteins and sequences encoding enzymes. Specific examples include green fluorescent protein (e.g., U.S. Pat. No. 5,422,266; Prasher D C et al. (1992) *Gene* 111:229-233; GenBank Accession No. I24081). Persons skilled in the art will readily be able to identify other examples of polynucleotides encoding detectable label using, for example, sequences publicly available from GenBank.

An aspect of the invention pertains to vectors, including expression vectors, containing a nucleic acid encoding a polypeptide of the invention. As used herein, the term "vector" refers to a nucleic acid molecule capable of transporting another nucleic acid to which it has been linked. One type of vector is a plasmid, which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequencers) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those which direct constitutive expression of a nucleotide sequence-in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic (e.g., *E. coli*) or eukaryotic cells (e.g., insect cells (using baculovirus expression vectors), yeast cells, or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc.; Smith and Johnson (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al. (1988) *Gene* 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS 174(DE3) from a resident lambda prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli*. Wada et al. (1992) *Nucleic Acids Res.* 20:2111-2118. Such alteration of nucleic acid sequences of the invention can be carried out by standard DNA synthesis techniques.

In another embodiment, the expression vector is a yeast expression vector. Examples of vectors for expression in yeast *S. cerivisae* include pYepSec1 (Baldari et al. (1987) *EMBO J* 6:229-234), pMFa (Kurjan and Herskowitz (1982) *Cell* 30:933-943), pJRY88 (Schultz et al. (1987) *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector, Examples of mammalian expression vectors include pCDM8 (Seed (1987) *Nature* 329:840) and pMT2PC (Kaufman et al. (1987) *EMBO J* 6:187-195). When used in mammalian cells, the expression vector's control functions are often provided by viral regulatory elements. For example, commonly used promoters are derived from polyoma, Adenovirus 2, cytomegalovirus (CMV) and Simian Virus 40 (SV40). For other suitable expression systems for both prokaryotic and eukaryotic cells see chapters 16 and 17 of Sambrook et al., eds., Molecular Cloning: A Laboratory Manual, 2nd ed., Cold Spring Harbor Laboratory, Cold Spring Harbor Laboratory Press, Cold Spring Harbor, N.Y., 1989).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (9387) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the beta-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—*Trends in Genetics*, Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic cell (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

Viral vectors, including but not limited to retroviruses, lentiviruses, adenoviruses, and adeno-associated viruses, can also be used to introduce DNA into cells.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce a polypeptide of the invention. Accordingly, the invention further provides methods for producing a polypeptide of the invention using the host cells of the invention. In one embodiment the method comprises culturing the host cell of invention (into which a recombinant expression vector encoding a polypeptide of the invention has been introduced) in a suitable medium such that the polypeptide is produced. In another embodiment, the method her comprises isolating the polypeptide from the medium or the host cell.

An aspect of the invention is a method for detecting cells undergoing cell death (e.g., apoptosis and necrosis). The method is based on detecting the uptake and retention by dying cells of a conjugate of a dehydrogenase and a detectable label, as described herein. The method of detection is selected so as to be appropriate for the particular detectable label that is incorporated into the conjugate. For example, gamma scintigraphy can be used to detect conjugates bearing a suitable gamma emitting detectable label. In one embodiment the cells to be detected by the method are cells undergoing apoptosis, which can include early-stage, late-stage, or a combination of early- and late-stage apoptosis. In one embodiment the cells to be detected by the method are cells undergoing necrosis. Of course in one embodiment the cells to be detected by the method are undergoing both apoptosis and necrosis.

In one embodiment, the method is performed in vitro. In this embodiment a population of cells in culture is contacted with the conjugate under conditions suitable for the cells to be able to take up the conjugate. These conditions are generally the same conditions as are suitable for maintaining cells in culture, i.e., physiological conditions, and they include an appropriate amount of time that is suitable to permit measurable uptake of conjugate by dying cells. As used herein, a "population of cells" refers to two or more cells, and more typically at least ten, at least one hundred, at least one thousand, or at least one million cells. The cells can be adherent or nonadherent (e.g., cells in suspension), and in one embodiment they are a block of tissue. An agent or condition that is known to induce apoptosis optionally can be applied to the cells, for example as a positive control. Alternatively or in addition, an agent or condition known to rescue cells from apoptosis optionally can be applied to the cells, for example as a negative control. Alternatively or in addition, an agent or condition suspected of being able to rescue cells from apoptosis optionally can be applied to the cells, for example as a test agent. In certain embodiments excess conjugate may be removed by one or more wash steps performed prior to the detecting. As disclosed herein, the conjugates of the invention are taken up by dying cells in a manner such that they do not wash away. Detection of the presence of label in the cells, particularly above a control or background level of uptake, indicates the presence of cells undergoing cell death. Conversely, absence of label detected in the cells, particularly as compared to a control or background level of uptake, indicates the absence of cells undergoing cell death.

This method can also be applied in a comparative manner so as to determine an increase or decrease in the degree or amount of cell death in a test population of cells as compared to a reference degree or amount of cell death in a reference population of cells. A "reference population of cells" refers to a population of cells similar in every respect to the test population of cells but for one variable of interest. For example, a reference population of cells can be from a healthy subject, whereas the test population of cells is from a diseased subject. Alternatively or in addition, the reference population of cells can be from an untreated subject, whereas the test population of cells is from a subject treated with a drug or agent of interest. The reference population of cells in one embodiment is a historical control for the test population of cells.

In one embodiment the cells used in the in vitro method are mammalian cells. In one embodiment the cells used in the in vitro method are human cells. In one embodiment the cells used in the in vitro method are cells obtained from a subject, for example for diagnosing or monitoring a condition of the subject, or for assessing the effect of a treatment of a condition of the subject.

Generally the in vitro methods involve contacting and detecting performed in vitro. In one embodiment, however, the contacting step can be performed in vivo and the detecting step performed in vitro.

Significantly, in one embodiment the method is performed entirely in vivo. In this embodiment the contacting involves administering the conjugate to a subject such that the conjugate comes in contact with a population of cells of interest within the subject. The administering can be accomplished by oral or parenteral administration, as may be appropriate for causing the conjugate to come into contact with the population of cells of interest within the subject.

The test population of cells can be cells of a subject having or suspected to have a condition associated with apoptosis. As used herein, a "subject" is any vertebrate. In one embodiment the subject is a mammal. In one embodiment the subject is a human. A "subject having a condition associated with apoptosis" is a subject diagnosed with such a condition or having at least one objective feature characteristic of a condition associated with apoptosis. A "subject suspected to have a condition associated with apoptosis" is a subject not yet diagnosed with such condition or suspected of having at least one objective feature characteristic of a condition associated with apoptosis.

As used herein, a "condition associated with apoptosis" is a condition such as a disease or disorder which has apoptosis as a feature characteristic of that condition. An important condition associated with apoptosis is cancer. Additional conditions associated with apoptosis include, without limitation, chemotherapy-, radiation-, or hormone-induced apoptosis in solid and hematological tumors; tumor resistance to therapy; acute cardiac allograft rejection; acute myocardial infarction; anthracycline-induced cardiotoxicity; arrhythmogenic right ventricle dysplasia; skeletal muscle apoptosis; congestive heart failure; coronary artery disease; atherosclerosis; infectious endocarditis; myocarditis; myocardial dysfunction; myocardial ischemia-reperfusion injury; non-cardiac allograft rejection; graft-versus-host disease; bacterial infection; viral infection; multiple organ dysfunction syndrome; septic shock; cerebral ischemia-reperfusion injury; macular degeneration; neurodegenerative disease; central nervous system trauma; autoimmune diabetes mellitus; rheumatoid arthritis; systemic lupus erythematosus; inflammatory bowel disease; multiple sclerosis; other autoimmune diseases; annexinopathies; osteoarthritis; renal failure; chronic renal atrophy and renal fibrosis; glomerular injury; and polycystic renal disease.

Cancer specifically includes solid malignant tumors and hematological malignancies as well as localized and metastatic cancer. Cancers include, but are not limited to, adenocarcinoma, basal cell carcinoma, biliary tract cancer; bladder cancer; bone cancer; brain and other central nervous system cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g., small cell and non-small cell lung cancer); lymphoma including Hodgkin's and Non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas.

Transplant rejection specifically includes but is not limited to acute and chronic immune-mediated rejection of kidney, heart, lung, liver, pancreas, small bowel, and skin allografts.

Neurodegenerative diseases specifically include but are not limited to Parkinson's disease, Alzheimer's disease, and Huntington's disease.

Central nervous system trauma specifically includes but is not limited to spinal cord injury and brain injury.

An aspect of the invention is a method for treating a condition associated with apoptosis. The method entails administering to a subject having or suspected to have a condition associated with apoptosis a pharmaceutical composition comprising a conjugate of a dehydrogenase linked to at least one therapeutic agent. The pharmaceutical composition includes a suitable conjugate of the invention in contact with a pharmaceutically acceptable carrier.

The term "pharmaceutically acceptable carrier" as used herein means one or more compatible solid or liquid fillers, diluents, or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The pharmaceutical composition is administered to the subject in an amount effective to treat the condition. As used herein, the term "treat" means to halt the progression of, to ameliorate, or to eliminate a condition. As used herein, the term "effective amount" is an amount that is sufficient to achieve a desired result. In the context of treating a condition, an effective amount is an amount sufficient to halt the progression of, to ameliorate, or to eliminate the condition.

Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is effective to treat the particular subject. The effective amount for any particular application can vary depending on such factors as the disease or condition being treated, the particular conjugate or composition of the invention being administered, the size of the subject, or the severity of the disease or condition. One of ordinary skill in the art can empirically determine the effective amount of a particular conjugate or composition of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate system levels can be determined by, for example, measurement of the patient's peak or sustained plasma level of the active compound. "Dose" and "dosage" are used interchangeably herein.

Generally, daily oral doses of active compounds will be from about 0.01 milligrams/kg per day to 1000 milligrams/kg per day. It is expected that oral doses in the range of 0.5 to 50 milligrams/kg, in one or several administrations per day, will yield the desired results. Dosage may be adjusted appropriately to achieve desired drug levels, local or systemic, depending upon the mode of administration. For example, it is expected that intravenous administration would be from an order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

For any conjugate or composition of the invention described herein the therapeutically effective amount can be initially determined from animal models. A therapeutically effective dose can also be determined from human data for conjugates or compositions of the invention which have been tested in humans and for compounds which are known to exhibit similar pharmacological activities, such as other related active agents. Higher doses may be required for parenteral administration. The applied dose can be adjusted based on the relative bioavailability so and potency of the administered compound. Adjusting the dose to achieve maximal efficacy based on the methods described above and other methods as are well-known in the art is well within the capabilities of the ordinarily skilled artisan.

In one embodiment the method of treatment further includes monitoring apoptosis in the subject. The monitoring can be performed using any suitable method capable of detecting apoptosis, including methods of the invention described herein. In various embodiments the monitoring can be performed in vitro or in vivo. Monitoring generally involves comparing apoptosis in the subject as measured on at least two occasions, e.g., before and after treatment. The monitoring thus can be performed to judge the effectiveness of a treatment and/or the status of a condition being treated. For example, dehydrogenase probes described herein are useful for evaluating the effectiveness of an anti-cancer treatment, such as an immunotherapy, a chemotherapy and a radiation therapy. As demonstrated in Examples 19 and 21 below, the invention provides a means to detect and visualize cell death in vivo induced by cancer therapeutics. Thus, the dehydrogenase probes described herein are useful as an indicator of drug efficacy in a condition that involves cell death (e.g., apoptosis and necrosis).

An aspect of the invention is a method for selectively delivering an agent to an apoptotic cell. The method is based on the ability of apoptotic cells to take up and retain a conjugate of dehydrogenase and an agent. The agent can be a diagnostic or therapeutic agent, as described herein, or it can be a test agent. In one embodiment the agent is an anti-apoptotic agent. The method involves contacting an apoptotic cell with a conjugate of the invention. The contacting can be accomplished in vitro or in vivo by any suitable method, provided the cell and the conjugate are brought into physical contact with one another. The conjugate is provided in an effective amount to achieve delivery of the agent to the cell.

An aspect of the invention is a method (screening assay) for identifying a modulator, i.e., an inducer or inhibitor, of apoptosis. In one embodiment the modulator identified by the method is an inhibitor of apoptosis, i.e., anti-apoptotic agent. In one embodiment the modulator identified by the method is a stimulator or inducer of apoptosis. The screening assay can be performed in vitro or in vivo.

In one embodiment, the invention provides assays for screening candidate or test compounds which modulate apoptosis. The test compounds of the present invention can be obtained using any of the numerous approaches in combinatorial and other molecular library methods known in the art, including: biological libraries and other natural product libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. Lam (1997) *Anticancer Drug Des* 12:145.

Examples of methods for the synthesis of molecular libraries can be found in the art, for example in: DeWitt et al. (1993) *Proc Natl Acad Sci USA* 90:6909; Erb et al. (1994) *Proc Natl Acad Sci US* 91:11422; Zuckermann et al. (1994) *J Med Chem* 37:2678; Cho et al. (1993) *Science* 261:1303; Carell T et al. (1994) *Angew Chem Int Ed Engl* 33:2059-2061; Carell T et al. (1994) *Angew Chem Int Ed Engl* 33:2061-2064; and Gallop et al. (1994) *J Med Chem* 37:1233.

Libraries of compounds may be presented in solution (e.g., Houghten (1992) *Bio/Techniques* 13:412-421), or on beads (Lam (1991) *Nature* 354:82-84), chips (Fodor (1993) *Nature* 364:555-556), bacteria (U.S. Pat. No. 5,223,409), spores (U.S. Pat. Nos. 5,571,698; 5,403,484; and 5,223,409), plasmids (Cull et al. (1992) *Proc Natl Acad Sci USA* 89:1865-1869) or phage (Scott and Smith (1990) *Science* 249:386-390; Devlin (1990) *Science* 249:404-406; Cwirla et al. (1990) *Proc Natl Acad Sci USA* 87:6378-6382; and Felici (1991) *J Mol Biol* 222:301-310).

In one embodiment, an assay is a cell-based assay in which a cell which is undergoing apoptosis or is subjected to apoptosis-inducing conditions is contacted with a test compound and the ability of the test compound to inhibit apoptosis determined. The cell, for example, can be a cell of mammalian origin. In one embodiment the cell is a human cell. Determining the ability of the test compound to inhibit apoptosis can be accomplished, for example, by using a conjugate labeled with a fluorescent, radioisotopic, or enzymatic label such that uptake of the label can be determined by detecting the labeled conjugate in the cell. For example, conjugates can be labeled with $^{125}I$, $^{35}S$, $^{14}C$, or $^3H$, either directly or indirectly, and the radioisotope detected by direct counting of radioemission or by scintillation counting. Alternatively, conjugates can be enzymatically labeled with, for example, horseradish peroxidase, alkaline phosphatase, or luciferase, and the enzymatic label detected by determination of conversion of an appropriate substrate to product.

In one embodiment, the assay comprises contacting the cell with a compound which is known to induce apoptosis, contacting the cell with a test compound, and determining the ability of the test compound to inhibit apoptosis, wherein determining the ability of the test compound to inhibit apoptosis comprises determining the uptake of conjugate by the cell in the presence of the test compound compared to the uptake of conjugate by the cell in the presence of the known compound alone. A reduced amount or degree of uptake of the conjugate by the cell in the presence of the test compound indicates the test compound is an inhibitor of apoptosis.

In one embodiment, the assay is a cell-based assay comprising contacting a cell that is not undergoing apoptosis or is not subjected to apoptosis-inducing conditions with a test compound and determining the ability of the test compound to stimulate or induce apoptosis. Determining the ability of the test compound to stimulate or induce apoptosis can be accomplished, for example, by determining the uptake of conjugate by the cell in the presence of the test compound compared to the uptake of conjugate by the cell in the absence of the test compound. An increased amount or degree of uptake of the conjugate by the cell in the presence of the test compound indicates the test compound is a stimulator or inducer of apoptosis.

In vitro screening methods of the invention can be adapted and performed as high-throughput screening assays. General methods for high-throughput screening assays are well known in the art and can include the use of samples presented in arrays, for example in multi-well plate format, that can be processed either manually or, conveniently, with automated or semi-automated sample and/or fluid handling devices adapted for use with a particular array format. For example, in one embodiment data are obtained using a 96-well format flow cytometer. In one embodiment high-throughput screening methods employ a high information content screening platform such as is commercially available from Cellomics (Thermo Fisher Scientific, Waltham, Mass.). The platforms in essence take a photomicrograph of each well of a 96- or 384-well multiplate, and then use image analysis to score for desired phentoypes (e.g., fluorescence, subcellular localization, etc.). In this case, a fluoresent LDH probe (or other suitable probe) can be added directly to the medium and directly scored since the dead cells will take up and concentrate the probe, which can be distinguished from the background fluorescence in the medium. No washing or change of medium would be necessary, in contrast to other probes (e.g., Annexin V). High-throughput screening methods generally permit screening of dozens, hundreds, even thousands of samples in a day.

For use in diagnosis and therapy, the conjugates of the invention are administered in pharmaceutically acceptable solutions, which may routinely contain pharmaceutically acceptable concentrations of salt, buffering agents, preservatives, compatible carriers, adjuvants, and optionally other therapeutic ingredients. Conjugates formulated in pharmaceutically acceptable solutions, whether for diagnostic or therapeutic use, are referred to herein as pharmaceutical compositions of the invention.

The pharmaceutical compositions of the invention contain an effective amount of a conjugate of the invention (or derivative thereof) and optionally one or more additional diagnostic or therapeutic agents included in a pharmaceutically acceptable carrier.

For use in diagnosis and therapy, an effective amount of the conjugate can be administered to a subject by any mode that delivers the conjugate to the desired surface. Administering the pharmaceutical composition of the invention may be accomplished by any means known to the skilled artisan. Routes of administration include but are not limited to oral, intravenous, intramuscular, intranasal, sublingual, intratracheal, inhalational, ocular, vaginal, and rectal.

For oral administration, the compounds (i.e., conjugates of the invention, and optionally other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark et al. (1982) *J Appl Biochem* 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the conjugate (or derivative) or by release of the biologically active material beyond the stomach environment, such as in the intestine.

To ensure fill gastric resistance, a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the conjugate (or derivative) may be formulated (such as by liposome or microsphere encapsulation) and then further contained within an edible product such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the conjugate or derivative either alone or as a mixture in different ratios.

Pharmaceutical preparations which can be used orally include push-fit capsules made of gelatin, as well as soft sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the conjugate and a suitable powder base such as lactose or starch.

Also contemplated herein is pulmonary delivery of the conjugates (or derivatives thereof). The conjugate (or derivative) is delivered to the lungs of a mammal while inhaling and traverses across the lung epithelial lining to the blood stream. Reports of other inhaled molecules include Adjei et al. (1990) *Pharmaceutical Research* 7:565-569; Adjei et al. (1990) *International Journal of Pharmaceutics* 63:135-144 (leuprolide acetate); Braquet et al. (1989) *Journal of Cardiovascular Pharmacology* 13(suppl. 5):143-146 (endothelin-1); Hubbard et al. (1989)*Annals of Internal Medicine* 3:206-212 (α1-antitrypsin); Smith et al. (1989) *J Clin Invest* 84:1145-1146 (α-1-proteinase); Oswein et al. (990) "Aerosolization of Proteins", In: Proceedings of Symposium on Respiratory Drug Delivery II, Keystone, Colo., March 1990, (recombinant human growth hormone); Debs et al. (1988) *J Immunol* 140: 3482-3488 (interferon-γ and tumor necrosis factor alpha); and U.S. Pat. No. 5,284,656 to Platz et al. (granulocyte colony stimulating factor). A method and composition for pulmonary delivery of drugs for systemic effect is described in U.S. Pat. No. 5,451,569, issued Sep. 19, 1995, to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the ACORN II® nebulizer, manufactured by Marquest Medical Products, Englewood, Colo.; the VENTOLIN® metered dose inhaler, manufactured by Glaxo Inc., Research Triangle Park, N.C.; and the SPINHALER® powder inhaler, manufactured by Fisons Corp., Bedford, Mass.

All such devices require the use of formulations suitable for the dispensing of conjugate (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified conjugate may also be prepared in different formulations depending on the type of chemical modification or the type of device employed.

Formulations suitable for use with a nebulizer, either jet or ultrasonic, will typically comprise conjugate (or derivative) dissolved in water at a concentration of about 0.1 to 25 mg of biologically active conjugate per mL of solution. The formulation may also include a buffer and a simple sugar (e.g., for conjugate stabilization and regulation of osmotic pressure). The nebulizer so formulation may also contain a surfactant, to reduce or prevent surface induced aggregation of the conjugate caused by atomization of the solution in forming the aerosol.

Formulations for use with a metered-dose inhaler device will generally comprise a finely divided powder containing the conjugate (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoro-ethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing conjugate (or derivative) and may also include a bulking agent such as lactose, sorbitol, sucrose, or mannitol in amounts which facilitate dispersal of the powder from the device, e.g., 50 to 90% by weight of the formulation. The conjugate (or derivative) should most advantageously be prepared in particulate form with an average particle size of less than 10 μM (micrometers), most preferably 0.5 to 5 μm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize an aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The conjugates, when it is desirable to deliver them systemically, can be formulated for parenteral administration by injection, e.g., by bolus injection or continuous infusion. Formulations for injection can be presented in unit dosage form, e.g., in ampoules, or in multi-dose containers, with an added preservative. The compositions can take such forms as suspensions, solutions or emulsions in oily or aqueous vehicles, and they can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds can be in powder form for constitution with a suitable vehicle, e.g., sterile pyrogen-free water, before use.

The compounds can also be formulated as rectal or vaginal compositions such as suppositories or retention enemas, e.g., containing conventional suppository bases such as cocoa butter or other glycerides.

In addition to the formulations described above, the compounds can also be formulated as a depot preparation. Such long-acting formulations can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer (1990) Science 249:1527-1533.

The conjugates and optionally other therapeutics may be administered per se (neat) or in the form of a pharmaceutically acceptable salt. When used in medicine, the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulfuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, such salts can be prepared as alkaline metal or alkaline earth salts, such as sodium, potassium, or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Particularly for sustained release formulations, the conjugate can be provided in particles. "Particles" as used herein means nano- or microparticles (or in some instances larger) which can consist in whole or in part of the conjugate or the other therapeutic agent(s) as described herein. The particles can contain the conjugate in a core surrounded by a coating, including, but not limited to, an enteric coating. The conjugate also can be dispersed throughout the particles. The conjugate also can be adsorbed into the particles. The particles can be of any-order release kinetics, including zero-order release, first-order release, second-order release, delayed release, sustained release, immediate release, and any combination thereof, etc. The particle can include, in addition to the conjugate, any of those materials routinely used in the art of pharmacy and medicine, including, but not limited to, erodible, non-erodible, biodegradable, or non-biodegradable material or combinations thereof. The particles can be microcapsules which contain the conjugate in a solution or in a semi-solid state. The particles can be of virtually any shape.

Both non-biodegradable and biodegradable polymeric materials can be used in the manufacture of particles for delivering the conjugate. Such polymers can be natural or synthetic polymers. The polymer is selected based on the period of time over which release is desired. Bioadhesive polymers of particular interest include bioerodible hydrogels described by Sawhney H S et al. (1993) *Macromolecules* 26:581-587, the teachings of which are incorporated herein. These include polyhyaluronic acids, casein, gelatin, glutin, polyanhydrides, polyacrylic acid, alginate, chitosan, poly(m-ethyl methacrylates), poly(ethyl methacrylates), poly(butyl-methacrylate), poly(isobutyl methacrylate), poly(hexyl-methacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The conjugate can be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as extended release) is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Labeling of LDH-B with Fluorescent Dyes $NH_2$ Group Modification:

Lactate dehydrogenase (LDH-B, mol wt 36 kDa) was obtained from Xpress Bio, MD. To synthesize Cy5.5-labeled LDH-B (Cy5.5-LDH-B), 0.2 µl dimethyl sulfoxide (DMSO) solution of Cy5.5 N-hydroxysuccinimide ester (0.18 µM) (Amersham-Pharmacia, Piscataway, N.J.) was added to 30 µg of LDH-B ($8.3 \times 10^{-4}$ µM) in 100 µl of 0.1M sodium bicarbonate, pH 8. The reaction was continued either for 120 minutes at room temperature or overnight at 4° C. The dye-labeled LDH-B was separated from unreacted dye molecules by spin separations using 2 ml of BioGel P6 columns in phosphate-buffered saline (PBS), pH 7.4 (Bio-Rad, Hercules, Calif.) as recommended. The concentration of protein and reacted Cy5.5 dye was determined by Nanodrop spectrophotometer. The concentration of dye was ~28 µM.

To synthesize fluorescein-labeled LDH-B (FITC-LDH-B), 30 µg of LDH-B in 100 µl of the buffer above was reacted with 0.18 µM of fluorescein isothiocyanate (FITC) for 2 hours at room temperature. The protein was separated from unreacted dye by spin separation, as above.

SH Group Modification:

In a typical reaction any amine-containing compound is reacted with succinimydil iodoacetate first to get the iodoacetate derivative of amine compound. The iodoacetate derivative is then reacted with LDH-B, where the thiol (—SH) group of amine reacts with the iodoacetate derivative.

Example 2

Direct Reaction of [$^{124}$I]NaI and [$^{125}$I] NaI with LDH Proteins

Fifty micrograms of LDH-B were dissolved in 1 mL of 0.1 mol/L phosphate buffer (pH 7.4) and reacted with 37 MBq $Na^{125}I$ in a V-vial (2-mL capacity; Pierce), the inner surface of which was coated with 100 µg 1,3,4,6-tetrachloro-3{alpha}6{alpha}-diphenylglycouril (IODO-GEN; Pierce). After gentle agitation of the vial for 15 min, the solution was removed from the vial, the vial was rinsed with 100 mL phosphate buffer, and the total solution was passed through a Millipore vented filter containing 1 g of Dowex 1×8, 100-200 mesh, chloride (Bio-Rad, Hercules, Calif.) or to a PD-10 column that had previously been blocked with bovine serum albumin (BSA) and washed with either binding buffer or PBS. The radio-labeled protein was eluted with either binding buffer or PBS and 0.5 ml fractions were collected.

Iodination with Water-Soluble Bolton-Hunter Reagent:

The reaction was performed in a glass vial because labeled LDH-B would adhere to the walls of polypropylene tubes. Water-soluble Bolton-Hunter reagent was dissolved in DMSO at 1.5 mmol/L (0.55 mg/mL). Ten microliters of chloramine-T (5 mg/mL in PBS) were added to $Na^{125}I$ (37 MBq) neutralized as above, in 10 µL PBS, followed by 1 µL water-soluble Bolton-Hunter reagent. The reaction was allowed to proceed for 1 min, stopped by the addition of 10 µL sodium metabisulfite (12 mg/mL in PBS), and immediate addition of the LDH-B (50 µg protein in 0.5 mol/L borate [pH 9.2]). After 1 h the reaction was stopped by the addition of 300 µL of 0.2 mol/L glycine in 0.2 mol/L borate (pH 8.0). LDH-B was purified by spinning repeatedly through a Microcon concentrator (Millipore, Bedford, Mass.). The same procedure was used to label BSA with $^{131}I$, except that after labeling the BSA was dialyzed overnight against 0.5% BSA in PBS.

Example 3

Radioactive Tc-Labeled LDH-B

HYNIC-derivatized LDH-B was produced by the gentle mixing of 5.6 mg/mL of LDH-B in 20 mmol HEPES, pH 7.4, 100 mmol NaCl for 3 h, shielded from light with succinimidyl 6-HYNIC (Anor MED Inc., Langley, British Columbia) [222 pg in 18.5 µL (42 mM) solution of N,N-dimethyl formamide] at room temperature. The reaction was quenched with 500 µL of 500-mmol glycine in PBS, pH 7.4, and then dialyzed at 4° C. against 20 mM sodium citrate, pH 5.2. 100 mM NaCl overnight. Precipitate was then removed by centrifuge at 15,000×g for 10 min. Ten microcuries of $^{99m}$Tc-glucoheptonate (DuPont, Wilmington, Del.) in 100 µL was incubated with a 100 µL (100 µg of protein) aliquot of HYNIC-derivatized LDH-B at room temperature for 1 h. After incubation the volume of reaction mixture was brought up to 1 mL with PBS, pH 7.4, with 0.1% human serum albumin (HSA) and collected in 1-mL fractions eluted from a Sephadex G-25 column (Pharmacia, Piscataway, N.J.) pre-rinsed with PBS/0.1% HSA.

Example 4

Metal Ion-Labeled LDH-B

LDH-B was reacted with DOTA-NHS ester (Macrocyclics, U.S.A.) in 0.1 M bicarbonate buffer at pH 8.0. It was then purified using a Bio-spin P6 column. The DOTA derivative was then reacted with $GdCl_3.6H_2O$ at pH 5.0-5.5 overnight by gradual addition of 1N NaOH solution. EDTA disodium salt was then added into the solution of chelate excess Gd ions. After stirring 30 min, the milky solution was purified with a Sephadex G-25 column to remove the EDTA-chelated Gd ions and the other unreacted low molecular weight compounds.

The DOTA-LDHB can also be coupled with other metals, e.g., radioactive Ga, Cu, In, Y, etc.

LDH-B is labeled with DTPA-PEG-NHS derivative, which after purification is chelated with the above-mentioned metallic ions. In a typical synthesis SCN-PEG-DTPA was synthesized by reaction of DTPA anhydride and $SCN-PEG-NH_2$. The SCN-PEG-DTPA was then reacted in 0.1 M bicarbonate buffer pH 8.5 with LDH-B at 4° C. overnight. Unreacted SCN-PEG-DTPA was removed using an AKTA fast-protein liquid chromatography system (Amersham Pharmacia Biotech) equipped with a Resource Q 1-mL anion-exchange column. The samples were eluted with 20 mmol/L Tris buffer (pH 7.5) and with a linear gradient of 0%-100% 1N NaCl in 15 mL at a flow rate of 4 mL/min.

To label DTPA-PEG-LDHB with $^{111}$In, a solution of DTPA-PEG-LDHB (200 μg/mL) in 20 mmol/L Tris buffer (pH 7.5) was incubated with 29.6 MBq (800 μCi) $^{111}$InCl$_3$ for 15 min.

Free $^{111}$In$^{3+}$ was removed by gel filtration from a PD-10 column eluted with PBS.

Example 5

$^{18}$F-Labeled LDH-B

Synthesis of 4-[$^{18}$F]Fluorobenzoic Acid:

Following the method of Torestsky J et al. (2004) *Nuclear Med Biol* 31:747-752, 50 to 100 μl of an aqueous solution of $^{18}$F$^-$ was transferred to a 5 ml conical screw-cap vial containing 1 ml dry acetonitrile, 5 mg kryptofix 222, and 8 μl 1 M K$_2$CO$_3$. The addition of 18F$^-$ marks the start of the time of synthesis. The reaction vial was heated at 95° C. and the liquid evaporated to a residue with a stream of nitrogen. The residue was dissolved in 300-500 μl dry acetonitrile and concentrated again under a stream of nitrogen to a residue. The azeotropic drying process was repeated twice more. To the residue was added a solution of 10 mg ethyl 4-(trimethylammonium triflate)benzoate dissolved in 200 μl dry N,N-dimethylacetamide; the vial was sealed and heated at 150° C. for 10 min. After cooling for two minutes, the hydrolysis step was carried out by the addition of 500 ml 1 M NaOH and a stir bar, followed by heating at 95° C. for 10 minutes, cooling for 2 min, and the addition of 800 ml 1 N HCl to make the reaction acidic (pH paper). The contents of the vial were drawn into a syringe and diluted to a final volume of 10 ml with water and loaded onto a Waters Sep-Pak™ that was activated by passing through it 30 ml acetonitrile followed by 30 ml water. The loaded Sep-Pak™ cartridge was washed with 2.0 ml 0.01 N HCl and blown dry for 10 min with a stream of nitrogen. Organic molecules including 4-fluorobenzoic acid were eluted with 2.5 ml acetonitrile. Injection of a sample of this fraction onto reverse-phase C18 radio-HPLC showed that the radioactivity eluted at the retention time of 4-fluorobenzoic acid.

Synthesis of N-Succinimidyl-4-Fluorobenzoate, [$^{18}$F]SFB:

The acetonitrile wash of the C18 Sep-Pak™ was transferred to a 25 ml round bottom flask. This was concentrated to a residue on a rotary evaporator using water aspirator vacuum and a room temperature heating bath. The residue was further dried by reconstitution in acetone followed by evaporation on the rotary evaporator, and repeating the addition of acetone and evaporation once more. The dry residue was dissolved in acetonitrile, transferred to a 5 ml screw cap conical vial and evaporated under a stream of nitrogen with no external heating. To the vial was added 50 μl 0.1 M dimethylamino-pyridine (DMAP) in acetonitrile and 200 μl 0.1 M N,N'-disuccinimidyl carbonate (DSC) (20 μmol) in acetonitrile; lower amounts of DSC gave incomplete conversion of 3 to [$^{18}$F]SFB. The vial was sealed, heated at 150° C. for 7-8 min, and cooled for 2 min. The contents of the vial were transferred to a 1.5 ml microfuge tube and 700 μl of water was added. The resulting suspension was centrifuged to pellet the precipitate, the supernatant removed, and injected onto a radio-HPLC (Delta-Pak-C18 column, 31μ, 3.9×155 mm; mobile phase—80% water/20% acetonitrile+0.1% glacial acetic acid; flow, 1 ml/min) and the radioactive peak eluting at 16 minutes collected. The HPLC eluate was diluted to a volume of 10 ml with water and loaded onto an activated Waters C18 Sep-Pak™. The Sep-Pak™ was blown dry with a stream of nitrogen for 10 min, and the [$^{18}$F]SFB was eluted with 2 ml methylene chloride. Recovery of [$^{18}$F]SFB from the Sep-Pak™ was essentially quantitative. The methylene chloride solution was evaporated to a visible residue under a stream of nitrogen.

Conjugation of [$^{18}$F]SFB to LDH-B:

The methylene chloride solution of [$^{18}$F]SFB was added to a 1.5 ml microfuge tube and evaporated to dryness under a gentle stream of nitrogen. To the residue in the tube was added 25-100 μl of a solution of LDH-B in 0.1 M borate buffer, pH 8.5 and incubated for 20 min at room temperature. The reaction was diluted to 400 μl with 0.1 M phosphate buffer, pH 7.4, and injected onto a TSK-G2000SWXL size exclusion column and eluted with 0.1 M phosphate buffer, pH 7.4 at a flow rate of 1.0 ml/min. Radioactive fractions were collected and radioactivity measured.

Example 6

Quantum Dots-Coupled LDH-B

Carboxyl-containing PEGylated quantum dots (Invitrogen) were dissolved in 10 mM borate buffer at pH 7.4. After adding an appropriate amount of LDH-B, an equivalent amount of 1-ethyl-3-[3-dimethylaminopropyl]carbodiimide hydrochloride (EDC) (Pierce) stock solution was added to it and stirred at room temperature for 2 hrs. The conjugate solution was filtered through a 0.2 μm PES syringe filter to remove any large aggregates and transfer the solution to a clean centrifugal ultrafiltration unit (100 kDa cutoff). The solution was centrifuged using 50 mM borate buffer, pH 8.3 to remove any excess unbound protein. The volume of concentration was >10-fold (e.g., 4 mL to <400 μL) each time. After ultracentrifugation was complete, the concentrate was filtered through a 0.2 μm syringe filter or a 0.8/0.2 μm combination syringe filter to remove any aggregates.

Example 7

Fluorescent Iron Oxide-Labeled LDH-B 1 ml of Feridex (11.2 mg/ml, Bayer Pharmaceuticals, Mass.) was added to a solution containing 1.6 ml of NaOH, 0.7 ml of double-distilled H$_2$O, and 0.7 ml of epichlorohydrin. The mixture was reacted for 12 hours with constant shaking. To produce reactive amines on the dextran coat, concentrated ammonia (0.5 ml) was added to the Feridex and reacted overnight at 37° C. Excess epichlorohydrin and ammonia were removed by extensive dialysis against water using 12,000-14,000 molecular weight cut-off tubing. The NH$_2$-Feridex nanoparticle at 0.2 ml at 10 mg Fe/ml in 0.02 M citrate (pH 8) was added to a tube of Cy5.5 (Amersham-Pharmacia) at room temperature for 2 h, with subsequent incubation at 4° C. overnight. It was then reacted with 120 mM succinimidyl 3-(2-pyridyldithio) propionate (SPDP) (Molecular Biosciences, Boulder, Colo.) dissolved in DMSO. After reaction for 2 hr at room temperature, low-molecular-weight impurities were removed by filtration through Sephadex G25F columns equilibrated with 20 mM Na-citrate buffer, pH 8.

To 1 μl of LDH-B (3 μg) was added 600 μl of 0.1 M sodium bicarbonate, pH 8.6, and 12 μl of 10.8 mM SATA (N-succinimidyl 3-(2-pyridylthio)propionate, S-acetylthioacetate) dissolved in DMSO. After 1 h at room temperature under argon, 220 µl of a solution of 0.01 M hydroxylamine, 0.01 M EDTA (pH 8) was added. The mixture was incubated for 40 min at room temperature under argon, and unreacted SATA separated from LDH-B by spin separation (Biogel P6 columns equilibrated with 0.1 M sodium bicarbonate, pH 8).

200 µl of 2Py-SS-Feridex-Cy5.5 was added to the SATAylated LDH-B and the mixture allowed to stand overnight at room temperature under argon. Unreacted LDH-B was removed by gel filtration (Sephadex G-150 equilibrated in 0.02 citrate 0.15 M NaCl, pH 8).

Example 8

Synthesis of LDH-Tri-Iodo Compound as CT Contrast Agent

The synthesis of triiodophthalamide derivative from Iobitridol (monomeric, non-ionic X-ray contrast medium based on tri-iodinated benzoic acid, brand name Xenetix) was made as previously described. Fu Y et al. (2004) *Bioconjugate Chem* 17:1043-1056. It was then coupled with LDH at a ratio where the coupled LDH will be water soluble.

Example 9

Cy5.5-Labeled LDH is Taken Up by Cells in Early- and Late-Stage Apoptosis

HeLa cells ($5 \times 10^5$ in 10 cm plates) maintained in DMEM with 10% FBS were contacted with 5 µM camptothecin to induce apoptosis. Cell staining by FITC-labeled Annexin V (Abcam, Cambridge, Mass.) or Cy5.5-labeled chicken LDH (1 µL) prepared as described in Example 1, was measured by fluorescence-activated cell sorting (FACS) analysis (with cells in annexin binding buffer (Abcam)) 12 h, 24 h, and 48 h later. Untreated HeLa cells served as negative controls.

Results are shown in FIG. 1. Both cells contacted with FITC-labeled Annexin V and cells contacted Cy5.5-labeled chicken LDH progressively stained positive over 48 h, indicating apoptosis. The proportion of apoptotic cells detected by Cy5.5-labeled chicken LDH was comparable to the corresponding proportion of apoptotic cells detected by FITC-labeled Annexin V.

Confocal microscopy analysis revealed a membranous staining pattern for cells stained with FITC-labeled Annexin V (Abcam, Cambridge, Mass.), whereas cells stained with Cy5.5-labeled LDH stained with a punctate cytoplasmic pattern.

In order to confirm that the uptake was dependent on the LDH rather than the fluorochrome, similar experiments were performed using HeLa cells contacted with Cy5.5-labeled Annexin V (Abcam) and FITC-labeled chicken LDH. Results from this experiment were essentially as described above for HeLa cells contacted with FITC-labeled Annexin V or Cy5.5-labeled chicken LDH.

To further rule out non-specific probe entry, cells were stained with cLDHB, and then washed with 6 changes of PBS. Despite extensive washing, cLDHB staining of cells was entirely stable. Together, these results demonstrate that binding of cLDHB occurs early in the apoptotic cascade, coincident with loss of membrane polarity, and that intracellular staining with cLDHB is stable and does not passively diffuse away.

Confocal microscopy analysis revealed a membranous staining pattern for cells stained with Cy5.5-labeled Annexin V, whereas cells stained with FITC-labeled LDH stained with a punctate cytoplasmic pattern.

This concordance in staining by Annexin V and cLDHB was observed across a variety of adherent and suspension cancer cell lines (e.g., HeLa, RS(4;11), THP-1, MDA-MB231), with apoptosis induced using a variety of agents (i.e., camptothecin, doxorubicin, histone deacetylase [HDAC] inhibitors). Concordant staining was also observed in non-transformed rat cardiomyocytes, in which apoptosis was induced with doxorubicin, a known cardiotoxic agent.

Example 10

Cy5.5-Labeled LDH is Not Taken Up by Cells Not Undergoing Apoptosis

RS4;11 is a MLL-AF4 fusion transcript-positive t(4;11) pre-B ALL cell line that is highly resistant to chemotherapy and radiation. In this experiment RS4;11 cells ($1 \times 10^6$) were treated with 50 nM NVP-LAQ824 (Novartis Pharma, Basel, Switzerland) for 24 h and then contacted with FITC-labeled Annexin V (Abcam, Cambridge, Mass.) or Cy5.5-labeled chicken LDH and analyzed by FACS as in Example 9. NVP-LAQ824 is a potent hydroxamic acid-derived histone deacetylase inhibitor that induces apoptosis in nanomolar concentrations in myeloid leukemia cell lines, multiple myeloma, and patient samples. Catley L et al. (2003) *Blood* 102:2615-22.

Figure 2:
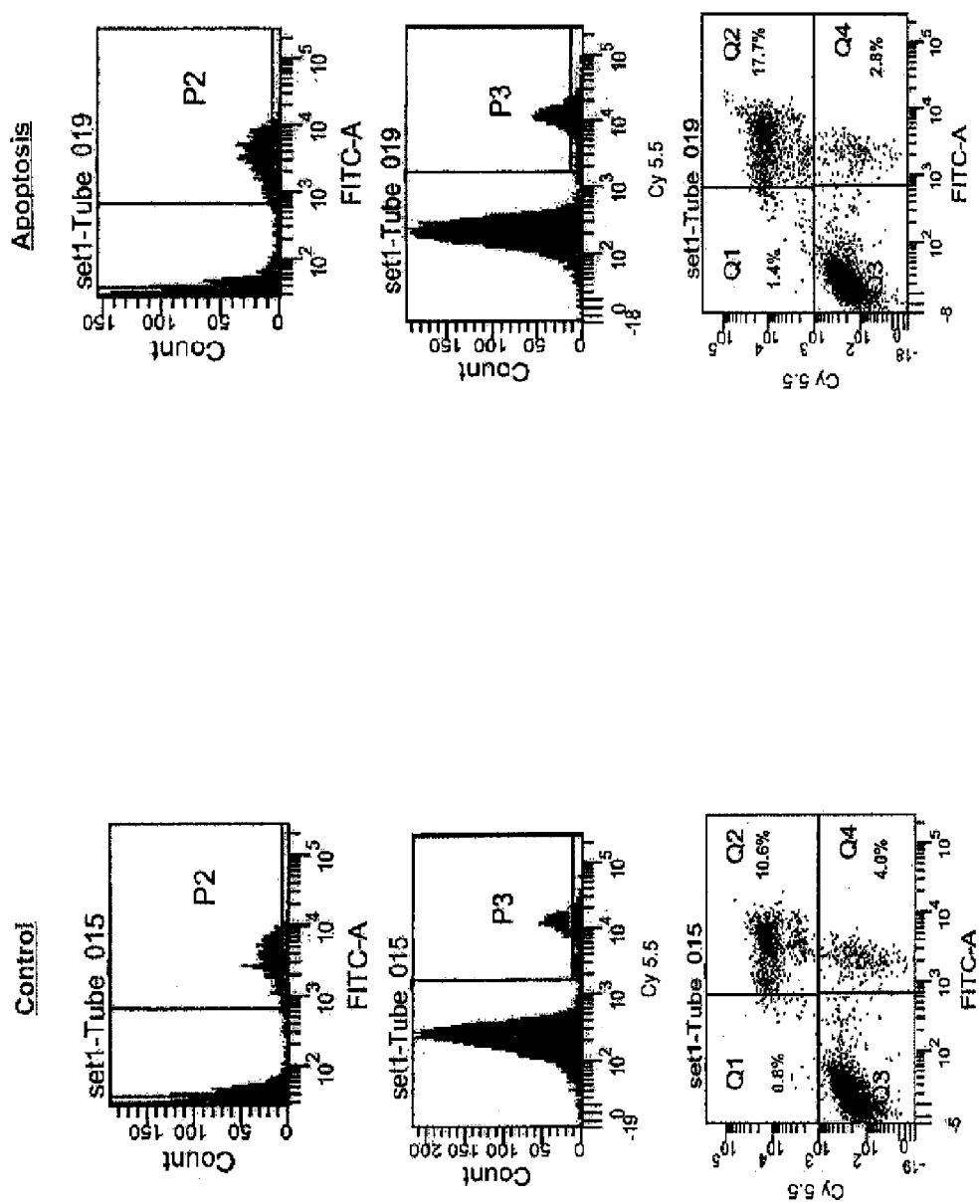
FIG. 2 is a collage of FACS histograms depicting apoptosis in RS4;11 cells as measured using FITC-labeled Annexin V and Cy5.5-labeled LDH.

Results are shown in FIG. 2. Treated RS4;11 cells had only a mild increase in apoptosis over background levels as measured with either FITC-conjugated Annexin V or Cy5.5-labeled LDH. However, in this case the staining was again comparable comparing Cy5.5-LDH to FITC-Annexin V. Together with results from Example 9, these results demonstrate that labeled LDH is taken up by apoptotic cells but not by non-apoptotic cells. Essentially identical results were obtained with different preparations of Cy5.5-labeled chicken LDH, and by conjugating LDH to FITC, demonstrating that the staining of apoptotic cells is mediated by LDH.

To correlate cLDHB staining with other measures of apoptosis, a fluorescent probe that binds to activated caspases (pan-caspase-FLICA, Immunochemistry Tech) was used. THP-1 cells were treated with the HDAC inhibitor LAQ824 (50 nM, 18 hrs) to induce apoptosis.

Identical to the results above, cLDHB-A680 staining was entirely coincident with caspase activation, and live cells negative for FLICA staining were likewise negative for cLDHB staining. These results demonstrate that cLDHB staining is concordant with both Annexin V-positivity and activation of caspases.

Example 11

LDH Uptake is Essentially Insensitive to Calcium

Staining by Annexin V is known to require the presence of calcium. This example shows that LDH, in contrast to Annexin V, is taken up by dying cells even in the absence of calcium. HeLa cells treated with camptothecin to induce apoptosis as in Example 9 were stained with FITC-labeled Annexin V (Abcam, Cambridge, Mass.) or Cy5.5-labeled chicken LDH in calcium-containing Annexin buffer or in calcium-free PBS. Stained cells were analyzed by FACS analysis as in Example 9.

Figure 3:
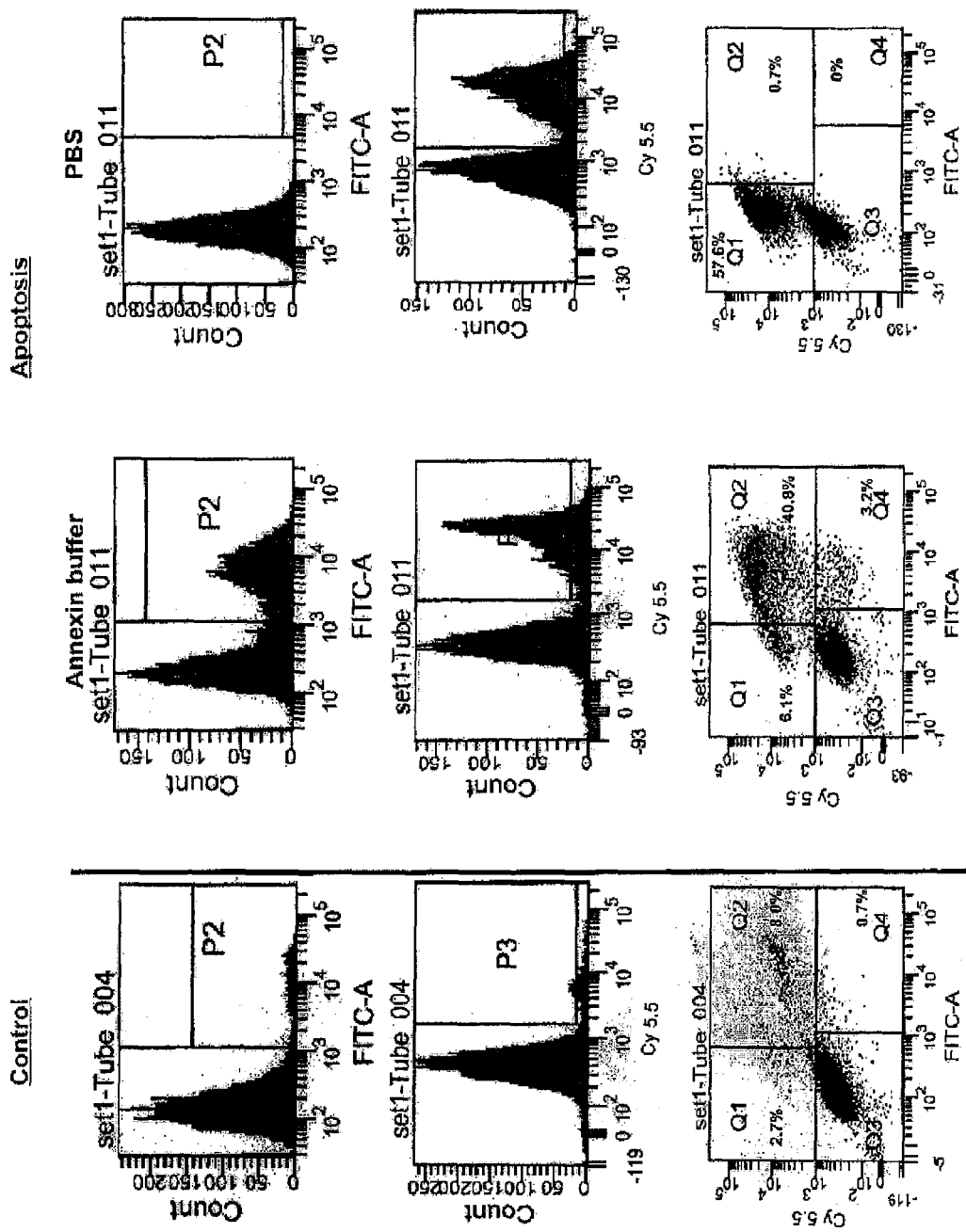
FIG. 3 is a collage of FACS histograms depicting apoptosis in HeLa cells as measured using FITC-labeled Annexin V and Cy5.5-labeled LDH in calcium-containing Annexin buffer or calcium-free phosphate-buffered saline (PBS).

Results are shown in FIG. 3. As shown in the figure, apoptotic cells stained with FITC-labeled Annexin V were strongly positive in Annexin V buffer but essentially not at all in PBS. In striking contrast, apoptotic cells stained with Cy5.5-labeled LDH were strongly and equally positive in Annexin V buffer and in PBS.

In a related experiment, RS4;11 cells were treated with 50 nM NVP-LAQ824 in culture media for 24 h and then stained with FITC-labeled Annexin V or A680-labeled human LDH-B in either Annexin buffer or culture media. Apoptosis was measured by FACS analysis. Results indicated a significant difference between 11-12 percent apoptotic cells as measured with FITC-labeled Annexin V in Annexin buffer versus only 4 percent apoptotic cells as measured with FITC-labeled Annexin V in culture media. In contrast, results indicated 11-12 percent apoptotic cells as measured with A680-labeled LDH-B, whether in Annexin buffer or culture media.

Example 12

LDH Probe Staining is Not Affected by Serum Proteins

HeLa cells ($5 \times 10^5$ in 10 cm plates) maintained in DMEM with 10% FBS were contacted with 5 µM camptothecin to induce apoptosis. Cell staining was done in the media: (i) annexin buffer, (ii) DMEM supplemented with 1% FBS; (iii) DMEM supplemented with 2% FBS; (iii) DMEM supplemented with 5% FBS; (iv) DMEM supplemented with 10% FBS. For cell staining FITC-labeled Annexin V (Abcam, Cambridge, Mass.) or Cy5.5-labeled chicken LDH (1 µL) prepared as described in Example 1, was used to for FACS analysis (cells in annexin binding buffer (Abcam)) 48 h later. Untreated HeLa cells served as negative controls.

Figure 4:
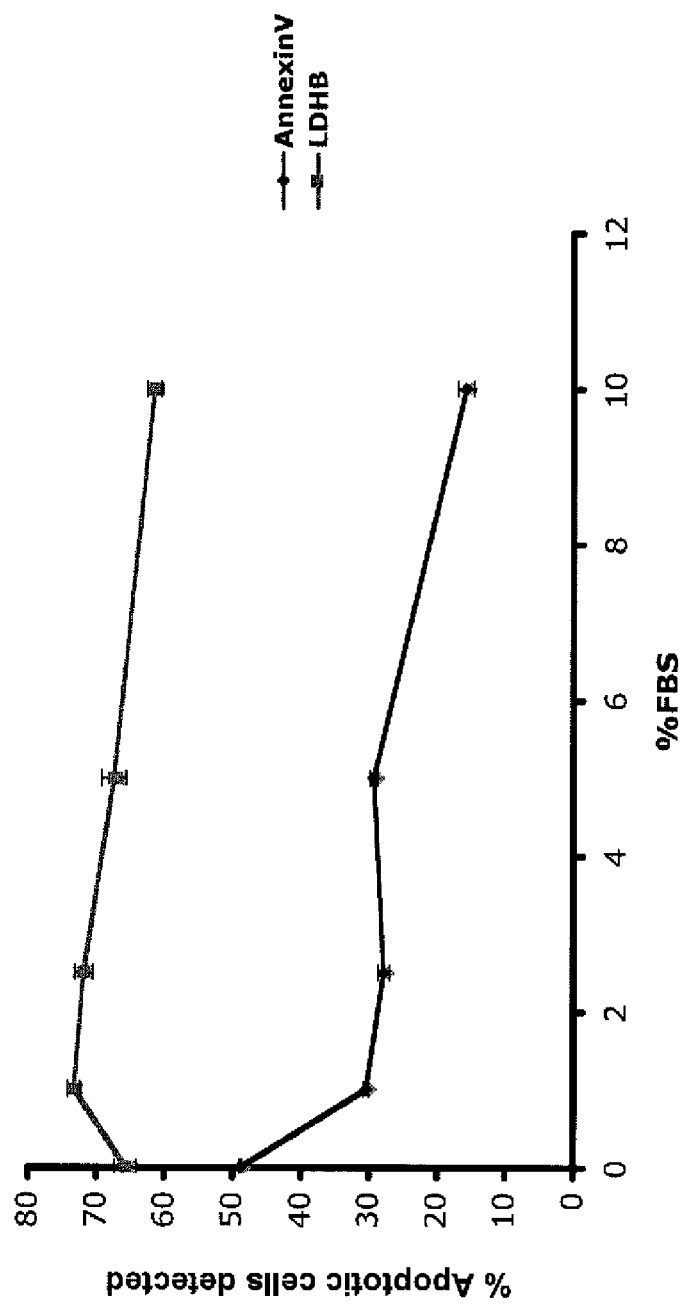
FIG. 4 is a graph depicting insensitivity of LDH-based apoptosis assay to serum as compared to Annexin V-based apoptosis assay.

Results are shown in FIG. 4. As can be seen from the figure, the percent apoptotic cells as measured with Annexin V decreased from about 50 percent to about 15 percent as the FBS increased from zero to 10 percent. In contrast, the percent apoptotic cells as measured with LDH-B was about 65 percent over the same range of FBS.

Example 13

LDH Staining Does Not Require ATP, Calcium, or Protein-Free Conditions

To determine if cLDHB is actively transported into cells, staining was performed at room temperature and at 4° C. Identical results were obtained in both conditions, suggesting that cLDHB entry into apoptotic cells is not an active ATP-dependent process.

A major limitation of Annexin V staining is the requirement for supra-physiological concentrations of calcium (Tait, J. F., D. F. Gibson, and C. Smith, *Anal Biochem,* 2004. 329: 112-9). To determine whether cLDHB staining required calcium, Annexin V and cLDHB staining was performed in PBS (without calcium or magnesium) or in Annexin Binding Buffer (with 2.5 mM calcium). Annexin V staining was significantly decreased in PBS compared to Annexin Binding Buffer, whereas cLDHB staining was identical under both conditions, demonstrating no requirement for calcium.

Annexin Binding Buffer is also a protein-free buffer, which raised the question as to whether the presence of serum proteins would affect Annexin V and cLDHB staining. Staining of HeLa cells treated with camptothecin was performed in the presence of increasing amounts of fetal bovine serum (FBS), and FACS was used to quantify staining. Whereas Annexin V staining was significantly decreased by increasing amounts of FBS, no significant changes were observed for cLDHB staining.

The lack of requirement for calcium and insensitivity to serum proteins suggested that cLDHB-based probes should be amenable for use in homogeneous assays. Indeed, apoptosis can be quantified in multiwell format by directly adding cLDHB probe to normal growth medium (e.g., RPMI with 10% FBS), followed by high-throughput analysis by flow cytometry (FACSCaliber with Multiwell Autosampler) or High-Content Microscopy. No Annexin V staining could be observed under these conditions.

Of note, typical staining protocols for Annexin V utilize a final probe concentration of 1 mg/ml (25 µM). For cLDHB-based probes, typically, concentrations of 0.1-0.5 µM may be used. Together, these results suggest that cLDHB has several advantages in comparison to Annexin V for detection of apoptotic cells, namely no requirement for calcium and no modulation by serum proteins. For in vitro applications, these characteristics make cLDHB highly facile for both routine analysis (e.g., FACS, microscopy) and in high-throughput applications (e.g., high-throughput screening). For in vivo imaging, these characteristics are also highly desirable since neither calcium nor serum proteins levels can be manipulated in preclinical models or humans.

Example 14

GST-LDH-A, GST-LDH-B, and GST-LDH-C Fusion Proteins, but Not GST Alone, are Taken Up by Dying Cells To determine whether fusion to LDH could target ectopic polypeptides to apoptotic cells, hLDHA, B, and C (38 kDa) were created as fusion proteins to GST (26 kDa). HeLa cells ($5 \times 10^5$ in 10 cm plates) maintained in DMEM with 10% FBS were contacted with 5 µM camptothecin to induce apoptosis. Cell staining by FITC-labeled Annexin V (Abcam, Cambridge, Mass.) or Cy5.5-labeled GST fusion of human LDHA, LDHB and LDHC (1 µL) prepared as described in Example 1, was measured by FACS analysis (cells in annexin binding buffer (Abcam)) 48 h later. Untreated HeLa cells served as negative controls. Unconjugated LDHB served as a positive control.

Glutathione S-transferase (GST), a non-dehydrogenase enzyme very similar in molecular weight to LDH, was conjugated with FITC. HeLa cells were contacted with 5 µM camptothecin to induce apoptosis, followed by staining with FITC-labeled GST as mentioned in Example 9.

Figure 5:
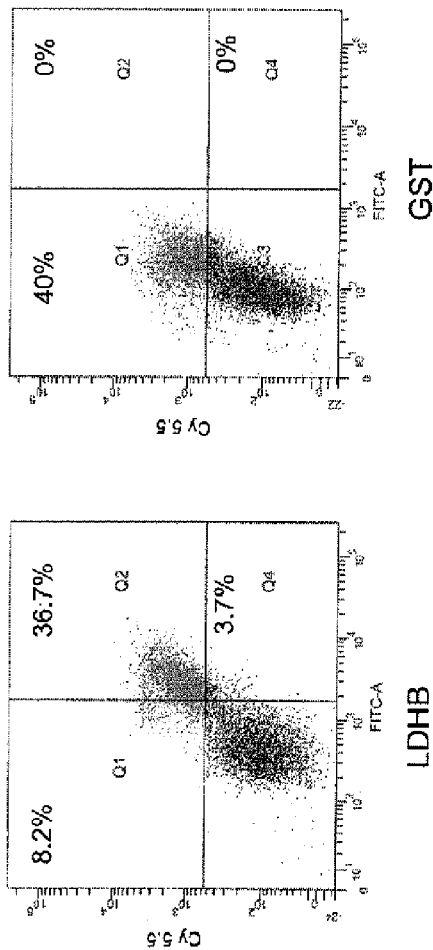
FIG. 5 is a collage of FACS histograms depicting that FITC-labeled glutathione S transferase (GST) failed to stain apoptotic HeLa cells, while FITC-labeled GST fusion proteins prepared with each of three isoforms of human LDH (LDH-A, LDH-B, and LDH-C) did stain apoptotic HeLa cells, as did unconjugated LDH-B probe.
Figure 5:
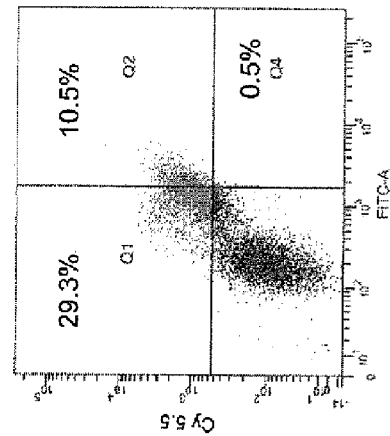
Figure 5:
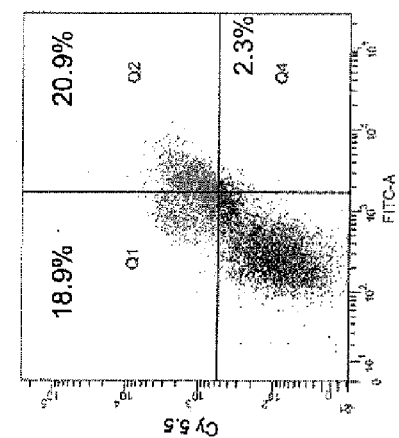
Figure 5:
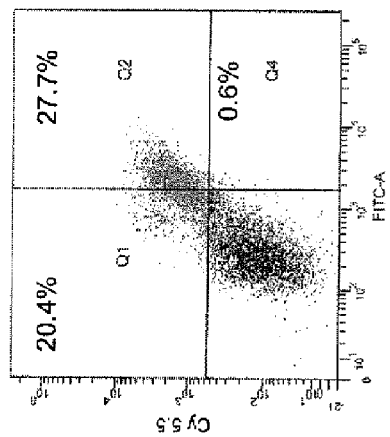

As shown in FIG. 5, labeled GST fusion proteins of LDH-A, LDH-B and LDH-C were taken up by apoptotic cells. In contrast to FITC-labeled LDH, apoptotic cells did not stain positive with FITC-labeled GST. Thus, whereas GST alone did not stain apoptotic cells, GST fused to LDHA, LDHB, and LDHC stained apoptotic cells similar to LDHB alone.

Similarly, we asked whether the fission proteins performed comparably to purified recombinant LDH. When THP-1 cells treated with a HDAC inhibitor (LAQ824, 50 nM, 18 hrs) were stained, we found that the GST-fused LDH subunits stained apoptotic cells comparably to isolated cLDHB and hLDHB cleaved and purified away from the GST moiety. These results demonstrate that hLDH subunits can carry at least a 26 kDa "payload" into apoptotic cells.

Example 15

Alcohol Dehydrogenase is Taken Up by Dying Cells

HeLa cells ($5 \times 10^5$ in 10 cm plates) maintained in DMEM with 10% FBS were contacted with 5 µM camptothecin to induce apoptosis. Cell staining by FITC-labeled Annexin V (Abcam, Cambridge, Mass.) or Cy5.5-labeled yeast ADH (1 µL) prepared as described in Example 1, was measured by FACS analysis (cells in annexin binding buffer (Abcam)) 12 h, 24 h, and 48 h later. Untreated HeLa cells served as negative controls.

Figure 6:
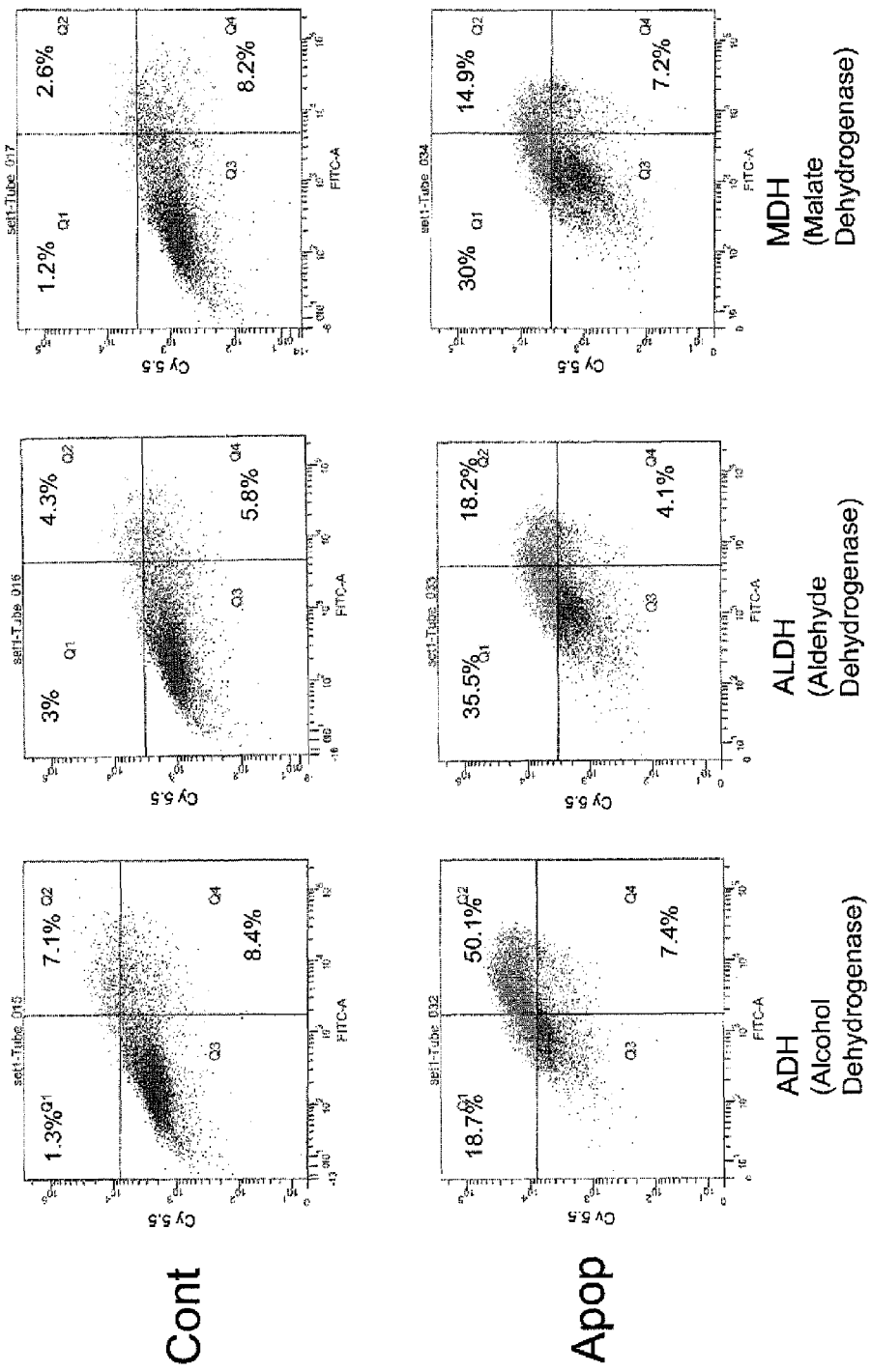
FIG. 6 is a collage of FACS histograms depicting detection of apoptotic HeLa cells with Alexa 680-labeled alcohol dehydrogenase (ADH), aldehyde dehydrogenase (ALDH), and malate dehydrogenase (MDH).

As shown in FIG. 6, labeled ADH was taken up by apoptotic HeLa cells, but not by control untreated HeLa cells.

Example 16

Aldehyde Dehydrogenase is Taken Up by Dying Cells

HeLa cells ($5 \times 10^5$ in 10 cm plates) maintained in DMEM with 10% FBS were contacted with 5 µM camptothecin to induce apoptosis. Cell staining by FITC-labeled Annexin V (Abcam, Cambridge, Mass.) or Cy5.5-labeled yeast ALDH (1 µL) prepared as described in Example 1, was measured by FACS analysis (cells in annexin binding buffer (Abcam)) 12 h, 24 b, and 48 h later. Untreated HeLa cells served as negative controls.

As shown in FIG. 6, labeled ALDH was taken up by apoptotic HeLa cells, but not by control untreated HeLa cells.

Example 17

Malate Dehydrogenase is Taken Up by Dying Cells

HeLa cells ($5 \times 10^5$ in 10 cm plates) maintained in DMEM with 10% FBS were contacted with 5 µM camptothecin to induce apoptosis. Cell staining by FITC-labeled Annexin V (Abcam, Cambridge, Mass.) or Cy5.5-labeled *E. coli* MDH (1 µL) prepared as described in Example 1, was measured by FACS analysis (cells in annexin binding buffer (Abcam)) 12 h, 24 h, and 48 h later. Untreated HeLa cells served as negative controls.

As shown in FIG. 6, labeled MDH was taken up by apoptotic HeLa cells, but not by control untreated HeLa cells, Example 18

Competition for Annexin V and LDHB Binding to Apoptotic Cells

To determine whether physiological levels of LDH may preclude binding of a LDH probe, the ability of excess unlabeled cLDHB and Annexin V to compete for binding of apoptotic cells by FITC conjugated Annexin V and cLDHB was assessed.

Apoptosis was induced in THP-1 cells with LAQ824 (50 nM, 18 hrs), and cells were stained with either Annexin V-FITC or cLDHB-FITC at a final concentration of 0.1 µM. For competition, staining was performed in the presence of excess unlabeled LDHB or Annexin V.

The ability of Annexin V-FITC to stain apoptotic cells was abrogated by a 5- and 10-fold excess of unlabeled Annexin V. Unlabeled Annexin V had no effect on LDHB-FITC staining. LDHB-FITC staining was only marginally altered by large excesses of unlabeled LDHB, up to 100-(10 µM) and 350-fold (35 µM) excess.

Of note, normal concentrations of LDH in human serum is ~0.03 µM (based on a normal range of 125-250 U/L, activity of 250-450 U/mg, and a molecular weight of 35 kDa). Patients with cancer may have LDH levels that are up to ~0.6 µM (1000-5000 U/L). In the case of mice, distribution of 20 µg of probe into a total blood volume of 2.5 ml would produce a probe concentration of 8 mg/L=~0.2 µM. Together these results demonstrate that LDHB probe staining is only mildly impacted by large excesses of LDH, far exceeding serum LDH levels even under pathological conditions.

Example 19

In Vivo Detection to Assess Effect of Taxol Treatment

For in vivo imaging, superficial orthotopic breast xenograft (MDA-MB435) tumors (5-10 mm) were established in mice. Animals were then treated with either Taxol 40 mg/kg or vehicle control by intravenous (IV) administration. After 24 hrs, a background image was obtained, then FL-LDH probe was injected IV. The animals were imaged immediately after probe injection and then at 0.5, 1, 2, 4, 8, 12, 24, and 48 hrs to establish probe kinetics within the tumors using a Caliper IVIS Spectrum instrument. As with most imaging probes, peak probe intensity occurred immediately after injection, but signal-to-noise (S:N) ratio increased as unbound probe was cleared from the blood.

In a second experiment, orthotopic breast xenograft (MDA-MB231) tumors (5-10 mm) were established in mice. Animals were then treated with either doxorubicin (adriamycin) 10 mg/kg or vehicle control by intravenous (IV) administration. After 36 hrs, a background image was obtained, then LDH-Cy5.5 probe was injected IV. The animals were imaged 24 h after probe injection using a Caliper IVIS Spectrum instrument.

Figure 7:
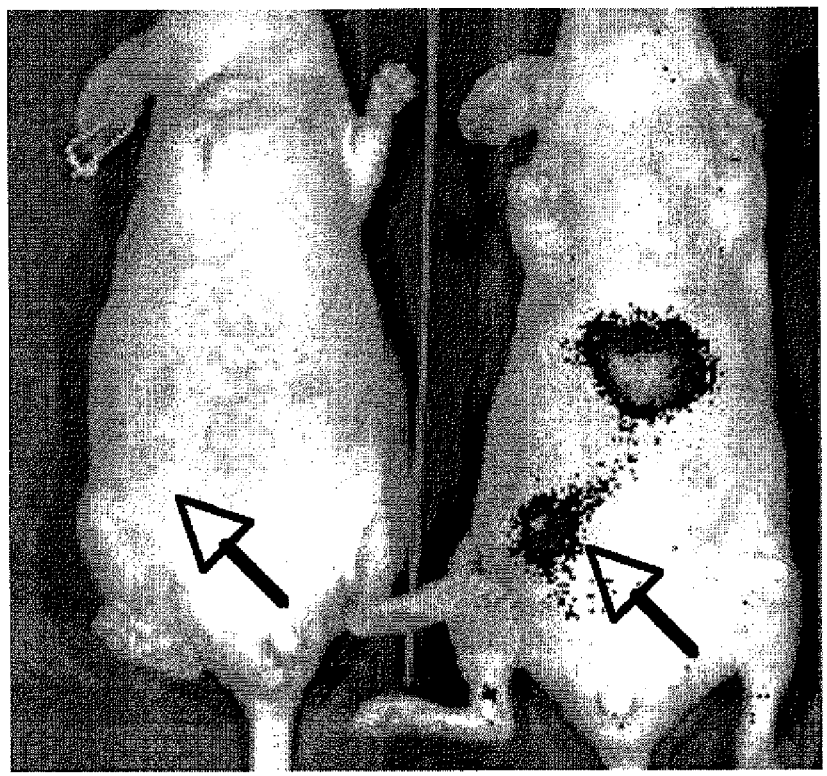
FIG. 7 is a pair of photographic images depicting accumulation of labeled LDH probe in mice, bearing orthotopic breast xenograft (MDA-MB435) tumors, treated with vehicle (left panel) or Taxol (right panel). Arrows indicate tumor position.

Results from the Taxol experiment are shown in FIG. 7. Localized probe accumulation in tumor (arrow) and liver was demonstrated in a Taxol-treated animal 48 hrs after probe injection. Results from the doxorubicin experiment showed similar accumulation of signal in tumor and in liver.

Studies of this kind are used to optimize probe dosing, imaging time, and fluorochrome/filter combinations.

Example 20

In Vivo Imaging of Fulminant Hepatic Failure

Figure 8A:
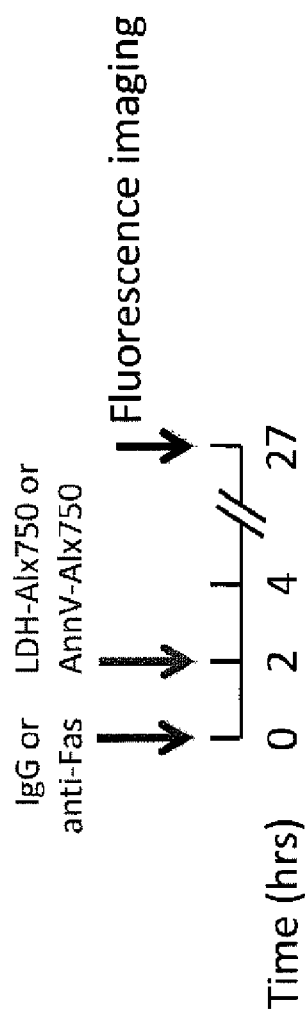
FIG. 8 provides an exemplary use of an LDH-B probe in a fulminant hepatic failure model. (A) provides a schema for treatment with anti-Fas or control IgG antibody and a series of images obtained from near-infrared in vivo imaging; (B, C) provide two graphs showing quantified results for LDHB probe and Annexin V probe in comparing anti-Fas treated animals to IgG control animals (n=5 per group).
Figure 8A:
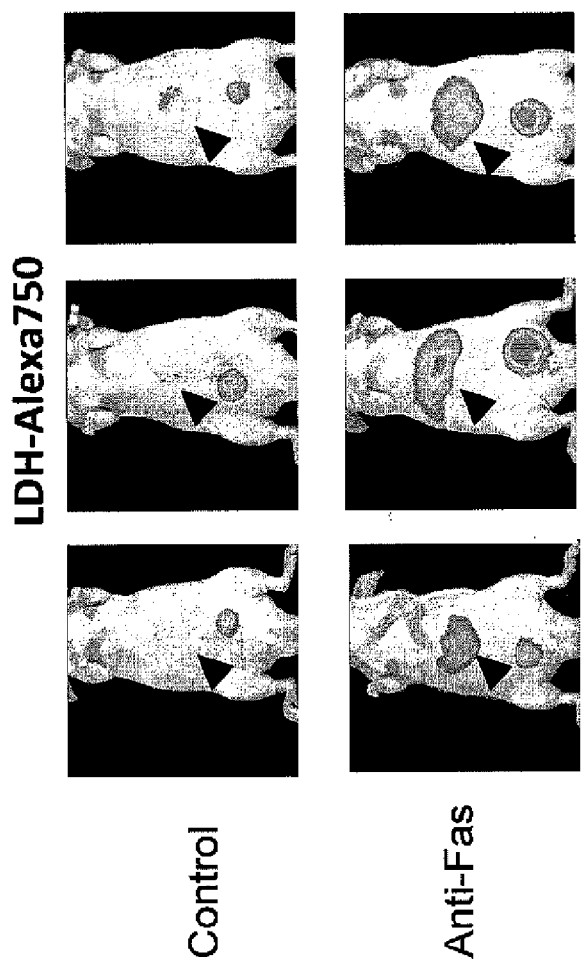

Hepatocyte apoptosis is rapidly induced in mice treated with an anti-Fas antibody (Chang, B. et al. *Arch Biochem Biophys*, 2003. 411: 63-72; Feng, G. and N. Kaplowitz, *J Clin Invest*, 2000. 105: 329-39; Nishimura, Y. et al., *Int Immunol*, 1997. 9: 307-16; Ogasawara, J. et al., *Nature*, 1993. 364: 806-9). This model was used to compare LDH to Annexin V for near infrared (NIR) imaging of apoptosis. Alexa750-NHS was conjugated to Annexin V (Biovision) and chicken LDHB (XpressBio) at a labeling ratio of 2:1 per mole of protein based on prior optimization. A total of 10 male NCr nude mice were injected with 5 µg of anti-Fas antibody (Jo2, Pharmingen), and 10 animals were injected with 5 µg of an isotype-matched control antibody. Two hours later, mice were injected with 10 µg of either LDH-Alexa750 or Annexin V-Alexa750. Mice underwent NIR fluorescence imaging (IVIS Spectrum, Caliper) 25 hrs after probe injection (FIG. 8A). After spectral unmixing and background subtraction (Living Images software package), regions of interest were used to quantify fluorescence localized to the liver region (FIG. 8A), as indicated with arrowheads.

Figure 8B:
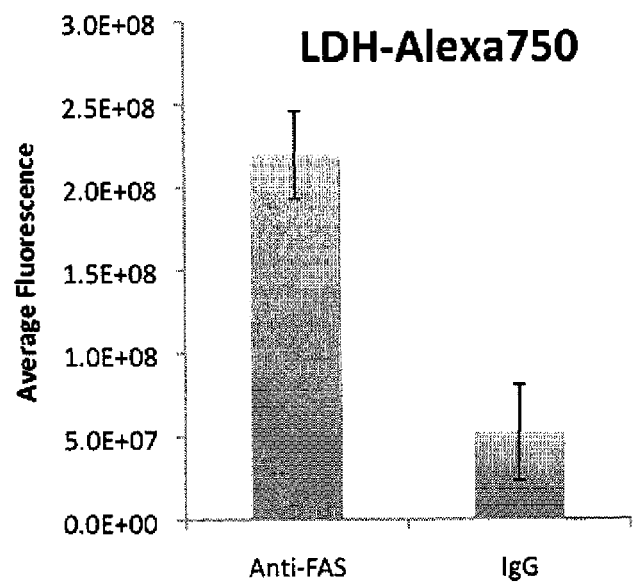
Figure 8C:
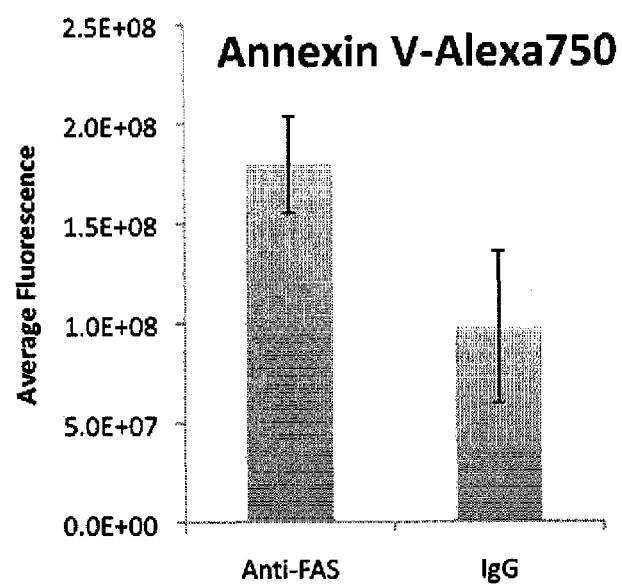

In mice injected with the LDH-Alexa750 probe, animals treated with anti-Fas antibody had mean signal intensity (photons/sec/ROI) that was 4.2-fold above animals treated with IgG control antibody (FIG. 8B). By comparison to an identically labeled probe, Annexin V-Alexa750 only resulted in a 1.8-fold signal increase in Anti-Fas antibody treated animals (FIG. 8C). These data support the hypothesis that several characteristics of LDH probes make it superior to Annexin V for detection of cell death in vivo.

Example 21

In Vivo Imaging of Chemotherapy-Induced Apoptosis

Targeted therapies such as imatinib, nilotinib and dasatinib have proven efficacy against BCR-ABL-dependent cells. Subcutaneous tumors were established using Ku812-Luc+ (BCR-ABL+CML blast crisis) cells in NCr nude mice. When tumors were ~1 cm, mice underwent bioluminescence imaging (BLI) to determine baseline tumor burden, followed by treatment with either AMN107 (nilotinib) at 100 mg/kg intraperitoneally (IP), or with vehicle. After 3 doses, animals were injected with 20 μg of LDH-Alexa750. Fluorescence imaging (FL) was performed 24 and 48 hrs after probe injection (day 4 and 5 of treatment) and BLI was repeated on day 5 of treatment (FIG. 9A).

Figure 9A:
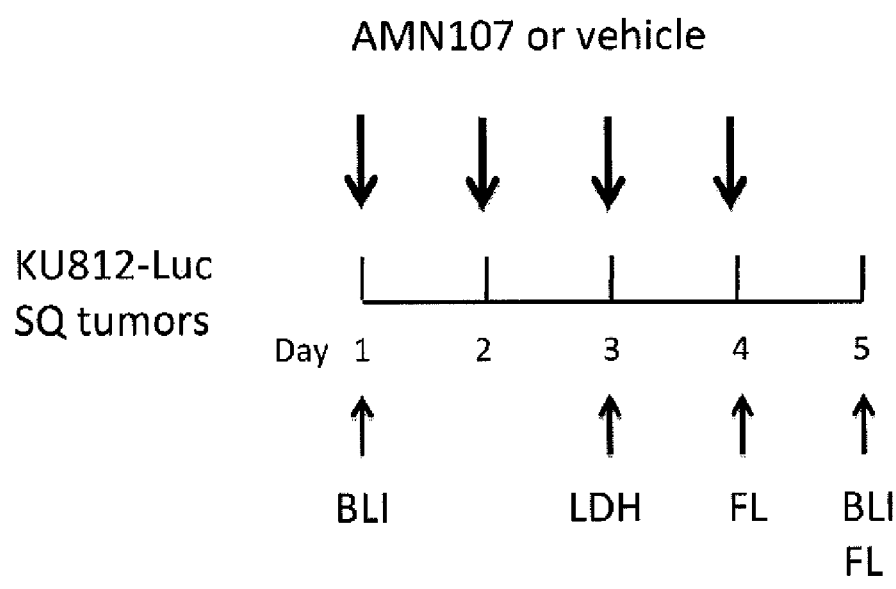
FIG. 9 provides an exemplary use of an LDH probe for imaging treatment-induced cell death. (A) depicts a schema for treatment of KU812 (BCR-ABL+) tumors with AMN107 (nilotinib) and a graph showing regression of tumors in AMN107-treated animals; (B, C) provide a series of images and a graph demonstrating increased uptake of LDHB probe in AMN107-treated animals by comparison to vehicle-treated controls. Arrowheads indicate tumor position.
Figure 9A:
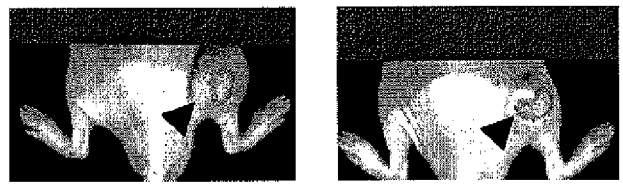
Figure 9A:
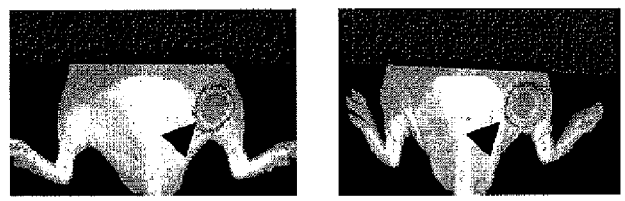
Figure 9B:
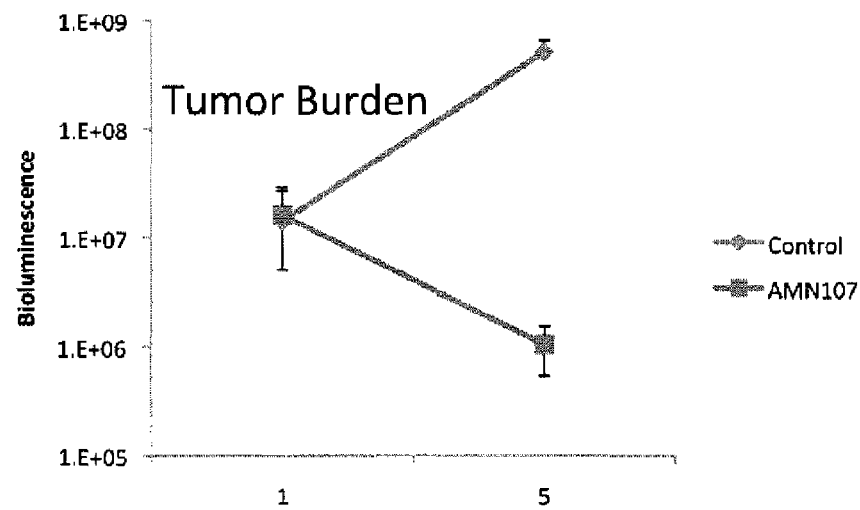
Figure 9C:
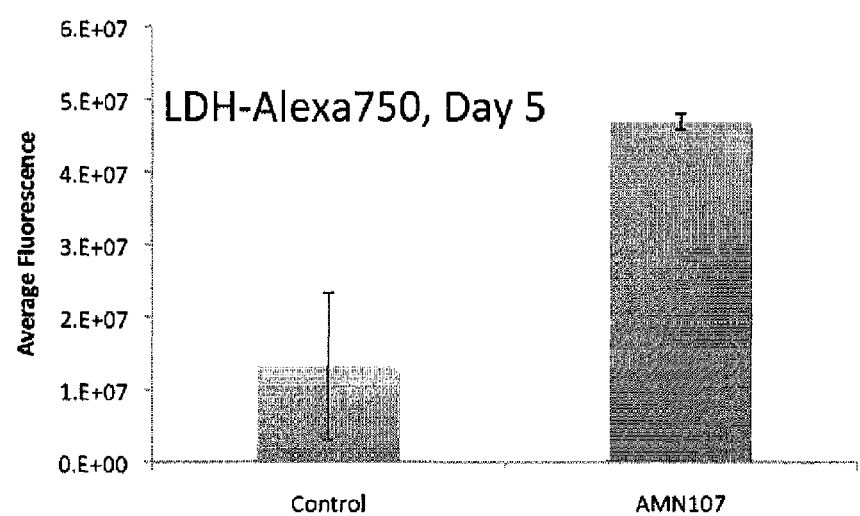

Treatment with AMN107 resulted in tumor regression and a 2-log difference between treated animals and vehicle-treated controls, as determined by BLI (FIGS. 9A & 9B). NIR fluorescence signal from the tumors was >4-fold higher in AMN107-treated animals compared to vehicle-treated controls (FIGS. 9A & 9C). The striking anti-tumor response in this model and the strong signal achieved in drug-treated animals demonstrate the ability of LDH-based probes to detect cell death in vivo.

The foregoing written specification is considered to be sufficient to enable one skilled in the art to practice the invention. The present invention is not to be limited in scope by examples provided, since the examples are intended as a single illustration of one or more aspects of the invention and other functionally equivalent embodiments are within the scope of the invention.

Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A method for detecting cells undergoing early apoptosis cell death, the method comprising:
   contacting a test population of cells with a conjugate of a dehydrogenase linked to a detectable label, under conditions suitable for uptake of the conjugate by the test population of cells, wherein the dehydrogenase is a lactate dehydrogenase (LDH), alcohol dehydrogenase (ADH), aldehyde dehydrogenase (ALDH) or malate dehydrogenase (MDH); and
   detecting the label in the test population of cells,
   wherein presence of the label in the test population of cells indicates cells undergoing early apoptosis.

2. The method of claim 1, wherein the lactate dehydrogenase (LDH) is LDH-A, LDH-B or LDH-C.

3. The method of claim 2, wherein the LDH is a human LDH.

4. The method of claim 1, wherein the dehydrogenase is a human dehydrogenase.

5. The method of claim 1, wherein the contacting and the detecting are carried out in vitro.

6. The method of claim 1, wherein the contacting and the detecting are carried out ex vivo.

7. The method of claim 1, wherein at least one of the contacting and the detecting is carried out in vivo.

8. The method of claim 7, wherein the contacting and the detecting are carried out in vivo.

9. The method of claim 1, wherein the test population of cells is obtained from a subject having or suspected of having a condition associated with apoptosis.

10. The method of claim 9, wherein the condition is selected from the group consisting of: cancer; chemotherapy-, radiation-, or hormone-induced apoptosis in solid and hematological tumors; tumor resistance to therapy; acute cardiac allograft rejection; acute myocardial infarction; anthracycline-induced cardiotoxicity; arrhythmogenic right ventricle dysplasia; skeletal muscle apoptosis; congestive heart failure; coronary artery disease; atherosclerosis; infectious endocarditis; myocarditis; myocardial dysfunction; myocardial ischemia-reperfusion injury; non-cardiac allograft rejection; bacterial infection; viral infection; multiple organ dysfunction syndrome; septic shock; cerebral ischemia-reperfusion injury; macular degeneration; neurodegenerative disease; central nervous system trauma; autoimmune diabetes mellitus; rheumatoid arthritis; systemic lupus erythematosus; inflammatory bowel disease; multiple sclerosis; autoimmune diseases; annexinopathies; osteoarthritis; renal failure; chronic renal atrophy and renal fibrosis; glomerular injury; and polycystic renal disease.

11. The method of claim 1, further comprising:
   measuring the amount of label detected in the test population of cells;
   comparing the amount of label detected in the test population of cells to a reference amount of label detected in a reference population of cells; and
   determining if (a) there is an increased amount of apoptosis when the amount of label detected in the test population of cells is greater than the reference amount of detected label, or (b) there is a decreased amount of apoptosis when the amount of label detected in the test population of cells is less than the reference amount of detected label.

* * * * *

SEQUENCE LISTING

```
<160> NUMBER OF SEQ ID NOS: 4

<210> SEQ ID NO 1
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 1

Asn Ala Ala Ile Arg Ser
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 2

Tyr Pro Tyr Asp Val Pro Asp Tyr Ala
1               5

<210> SEQ ID NO 3
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 3

Asp Glu Val Asp
1

<210> SEQ ID NO 4
<211> LENGTH: 28
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Wherein Xaa can be any amino acid
```

```
<220> FEATURE:
<221> NAME/KEY: misc_feature
<222> LOCATION: (2)..(3)
<223> OTHER INFORMATION: Wherein Xaa can be any amino acid
<220> FEATURE:
<221> NAME/KEY: misc_feature
<222> LOCATION: (5)..(10)
<223> OTHER INFORMATION: Wherein Xaa can be any amino acid
<220> FEATURE:
<221> NAME/KEY: misc_feature
<222> LOCATION: (12)..(14)
<223> OTHER INFORMATION: Wherein Xaa can be any amino acid
<220> FEATURE:
<221> NAME/KEY: misc_feature
<222> LOCATION: (16)..(20)
<223> OTHER INFORMATION: Wherein Xaa can be any amino acid
<220> FEATURE:
<221> NAME/KEY: misc_feature
<222> LOCATION: (22)..(27)
<223> OTHER INFORMATION: Wherein Xaa can be any amino acid

<400> SEQUENCE: 4

Cys Xaa Xaa Cys Xaa Xaa Xaa Xaa Xaa Xaa Trp Xaa Xaa Xaa Asp Xaa
1               5                   10                  15

Xaa Xaa Xaa Xaa His Xaa Xaa Xaa Xaa Xaa Xaa Cys
            20                  25
```